United States Patent
Masuda et al.

(10) Patent No.: US 8,896,846 B2
(45) Date of Patent: Nov. 25, 2014

(54) REFLECTIVE OPTICAL SENSOR AND IMAGE FORMING APPARATUS

(71) Applicants: Koji Masuda, Kanagawa (JP); Hidemasa Suzuki, Tokyo (JP)

(72) Inventors: Koji Masuda, Kanagawa (JP); Hidemasa Suzuki, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 66 days.

(21) Appl. No.: 13/845,462

(22) Filed: Mar. 18, 2013

(65) Prior Publication Data

US 2013/0216267 A1 Aug. 22, 2013

Related U.S. Application Data

(62) Division of application No. 12/859,373, filed on Aug. 19, 2010, now Pat. No. 8,422,033.

(30) Foreign Application Priority Data

Aug. 20, 2009 (JP) ................. 2009-190663

(51) Int. Cl.
*G01B 11/14* (2006.01)
*G01N 21/55* (2014.01)
*G03G 15/01* (2006.01)
*G03G 15/16* (2006.01)
*G03G 15/00* (2006.01)
*G03G 15/04* (2006.01)

(52) U.S. Cl.
CPC ............... *G03G 15/04* (2013.01); *G01N 21/55* (2013.01); *G03G 15/0131* (2013.01); *G03G 15/161* (2013.01); *G03G 2215/00616* (2013.01); *G03G 2215/0161* (2013.01); *G03G 15/5058* (2013.01); *G03G 2215/00059* (2013.01)

USPC .......................................... 356/614; 356/620

(58) Field of Classification Search
CPC ... G01N 21/55; G03G 15/04; G03G 15/0131; G03G 15/161; G03G 15/5058; G03G 2215/00059; G03G 2215/00616; G03G 2215/0161
USPC .................... 356/614–616, 619–624; 399/49, 399/301–302, 308, 60, 72; 347/116
See application file for complete search history.

(56) References Cited

U.S. PATENT DOCUMENTS

| 5,875,051 A | 2/1999 | Suzuki et al. |
| 5,986,791 A | 11/1999 | Suzuki et al. |
| 6,069,724 A | 5/2000 | Hayashi et al. |
| 6,075,638 A | 6/2000 | Masuda |
| 6,081,386 A | 6/2000 | Hayashi et al. |
| 6,141,133 A | 10/2000 | Suzuki et al. |
| 6,222,662 B1 | 4/2001 | Suzuki et al. |
| 6,259,546 B1 | 7/2001 | Masuda |
| 6,376,837 B1 | 4/2002 | Itabashi et al. |

(Continued)

FOREIGN PATENT DOCUMENTS

| JP | 64-35466 A | 2/1989 |
| JP | 8-6446 A | 1/1996 |

(Continued)

*Primary Examiner* — Tri T Ton
(74) *Attorney, Agent, or Firm* — Dickstein Shapiro LLP

(57) ABSTRACT

A reflective optical sensor includes at least three light-emitting elements; a lighting optical system that guides light emitted from the light-emitting elements to a toner pattern; and at least three light-receiving elements that receive the beams of light reflected by the toner pattern. The lighting optical system has a lateral magnification m that satisfies $m \leq P/S$, where S is the size of the light-emitting elements and P is the arrangement pitch of the light-emitting elements.

12 Claims, 35 Drawing Sheets

(56) References Cited

U.S. PATENT DOCUMENTS

| | | |
|---|---|---|
| 6,384,949 B1 | 5/2002 | Suzuki |
| 6,456,314 B1 | 9/2002 | Masuda |
| 6,462,879 B2 | 10/2002 | Masuda |
| 6,496,214 B1 | 12/2002 | Masuda et al. |
| 6,686,946 B2 | 2/2004 | Masuda et al. |
| 6,697,181 B2 | 2/2004 | Masuda |
| 6,717,606 B2 | 4/2004 | Masuda |
| 6,724,414 B2 | 4/2004 | Masuda et al. |
| 6,847,472 B2 | 1/2005 | Masuda |
| 6,858,859 B2 | 2/2005 | Kusunose |
| 7,068,295 B2 | 6/2006 | Masuda |
| 7,450,283 B2 | 11/2008 | Masuda |
| 7,593,150 B2 | 9/2009 | Masuda |
| 7,619,795 B2 | 11/2009 | Masuda |
| 7,655,936 B2 | 2/2010 | Sawayama et al. |
| 7,705,868 B2 | 4/2010 | Masuda et al. |
| 2005/0093963 A1 | 5/2005 | Masuda |
| 2007/0146473 A1 | 6/2007 | Masuda |
| 2008/0084594 A1 | 4/2008 | Masuda |
| 2009/0015896 A1 | 1/2009 | Masuda |
| 2009/0238590 A1 | 9/2009 | Masuda |
| 2010/0008686 A1 | 1/2010 | Masuda et al. |

FOREIGN PATENT DOCUMENTS

| | | |
|---|---|---|
| JP | 2000-241726 A | 9/2000 |
| JP | 2002-72612 | 3/2002 |
| JP | 2002-328099 A | 11/2002 |
| JP | 2004-21164 A | 1/2004 |
| JP | 2004-309292 A | 11/2004 |
| JP | 2005-238584 A | 9/2005 |
| JP | 2008-276010 A | 11/2008 |

B > P

B < P

REFLECTIVE OPTICAL SENSOR AND IMAGE FORMING APPARATUS

CROSS-REFERENCE TO RELATED APPLICATIONS

This is a divisional of U.S. patent application Ser. No. 12/859,373, filed Aug. 19, 2010. The entire disclosure of U.S. patent application Ser. No. 12/859,373 is incorporated herein by reference. The present application claims priority to and incorporates by reference the entire contents of Japanese Patent Application No. 2009-190663 filed in Japan on Aug. 20, 2009.

BACKGROUND OF THE INVENTION

1. Field of the Invention

The present invention relates to a reflective optical sensor and an image forming apparatus and, more particularly, to a reflective optical sensor that detects at least one of the position and the toner density of a toner pattern and an image forming apparatus that includes the reflective optical sensor.

2. Description of the Related Art

Well-known image forming apparatuses that form images using toner include copiers, printers, plotters, facsimile machines, and multifunction printers (MFPs). Such image forming apparatuses form a latent image on the surface of a drum-shaped photosensitive element and develop the latent image into a "toner image" by attaching toner to the latent image.

To form a good toner image, it is necessary to develop the latent image with an appropriate amount of toner. Various development techniques are known, such as a technique using "a two-component-based developer containing toner and carrier" and a technique using "mono toner" in which a developer containing only toner is used. The amount of toner to be supplied to a developing unit for developing the latent image is called "toner density".

If the toner density is insufficient, because the latent image cannot receive a sufficient amount of toner, an image (output image) with an insufficient density is output from the image forming apparatus. If the toner density is too high, the distribution of the density of the output image shifts toward being high density and an image difficult to recognize is formed. To form a good output image, it is necessary to set the toner density within an appropriate range.

A technique is widely used for adjusting the toner density to within an appropriate range, this technique involving forming a toner-density detection pattern, irradiating the pattern with light (detection light), and determining a change in the intensity of received light (see, for example, Japanese Patent Application Laid-open No. H1-35466, Japanese Patent Application Laid-open No. 2004-21164, Japanese Patent Application Laid-open No. 2002-72612, Japanese Patent No. 4154272, and Japanese Patent No. 4110027).

Conventional sensors that are used to detect the toner density include one or two light-emitting elements or three light-emitting elements, each having different characteristic wave length, and one or two light-receiving elements that receive reflected light. The length of the toner pattern is set to from 15 mm to 25 mm in the main direction so that, even if the position of the toner pattern is incorrect with respect to the sensor, the entire spot of the detection light can illuminate the toner pattern.

With the improvement of color image formation and high speeds in the field of image forming apparatuses, tandem-type image forming apparatuses have become widely used that include a plurality of (four, in general) drum-shaped photosensitive elements.

In such an image forming apparatus, if the positional relation is incorrect between the toner images formed on the photosensitive elements, an output image with a color shift is formed. A technique is widely used for adjusting the positional relation between the toner images, this technique involving forming a position detection pattern, irradiating the pattern with light (detection light), and detecting the position of the pattern using a temporal change in the intensity of reflected light (see, for example, Japanese Patent Application Laid-open No. 2008-276010, and Japanese Patent Application Laid-open No. 2005-238584).

It is noted that during a period when the toner-density detecting process and the pattern-position detecting process are performed, an image forming apparatus cannot perform its primary process, i.e., formation of an image to be output. A toner-density detecting process and a pattern-position detecting process using a conventional reflective optical sensor need a long time to form detection patterns, which reduces the efficiency of the primary process, i.e., formation of an image to be output.

Toner used for detection patterns is so-called "non-contributing toner" because such toner does not contribute to the primary process, i.e., formation of an image to be output. An increase in the amount of the toner used for detection patterns shortens time for replacement of the cartridge containing the toner.

SUMMARY OF THE INVENTION

It is an object of the present invention to at least partially solve the problems in the conventional technology.

According to an aspect of the present invention there is provided a reflective optical sensor configured to detect at least one of a position of the toner pattern or a toner density of a toner pattern. The reflective optical sensor includes: a light-emitting system that includes at least three light-emitting elements; a light-receiving system that includes at least three light-receiving elements and receives light emitted from the light-emitting system and then reflected by the toner pattern; and a lighting optical system that guides light emitted from the light-emitting system to the toner pattern. The at least three light-emitting elements and the at least three light-receiving elements are arranged at equal intervals in a certain direction. The lighting optical system has a lateral magnification m that satisfies m≤P/S, where S is size of the light-emitting elements and P is arrangement pitch of the light-emitting elements.

According to another aspect of the present invention there is provided an image forming apparatus including: an image carrier; an optical scanning device that scans the image carrier with a beam of light in a main-scanning direction, thereby forming a latent image, wherein the beam of light is modulated in accordance with image data; a developing device that forms a toner image by attaching toner to the latent image; a transferring device that transfers the toner image onto a medium; a reflective optical sensor that detects at least one of a position of or a toner density of a toner pattern on the image carrier or the medium. The reflective optical sensor includes: a light-emitting system that includes at least three light-emitting elements arranged at equal intervals in a certain direction; a lighting optical system that guides light emitted from the light-emitting system to the toner pattern; a light-receiving system that includes at least three light-receiving elements arranged at equal intervals in the certain direction, wherein the light-receiving system receives light reflected from the toner pattern. The lighting optical system is arranged so that $L/L_0<P/S$ is satisfied, where $L_0$ is distance between the light-emitting system and the lighting optical system, L is distance between the lighting optical system and the image carrier when the toner pattern on the image carrier is detected; or L is distance between the lighting optical system and the medium when the toner pattern on the medium is detected, S is size of the light-emitting elements, and P is arrangement pitch of the light-emitting elements.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
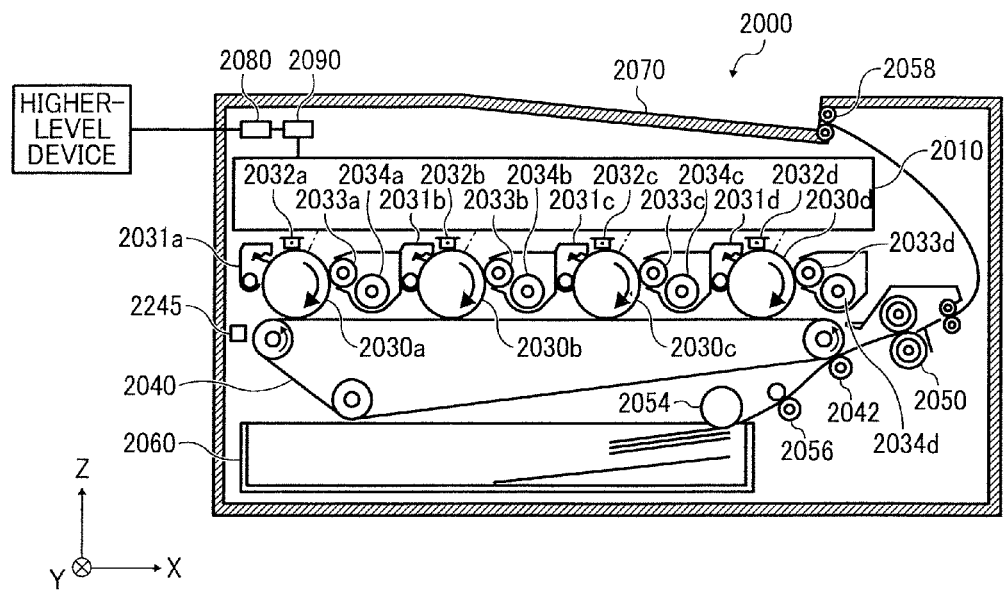
FIG. 1 is a schematic diagram of the configuration of a color printer according to an embodiment of the present invention.
Figure 2:
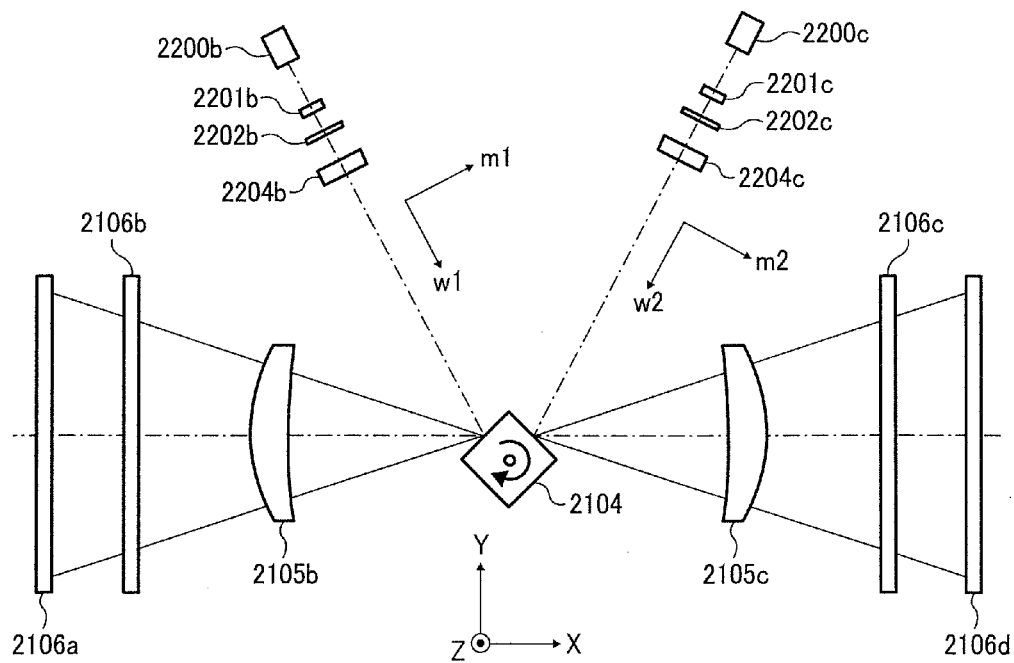
FIG. 2 is a first schematic diagram of the configuration of an optical scanning device.
Figure 3:
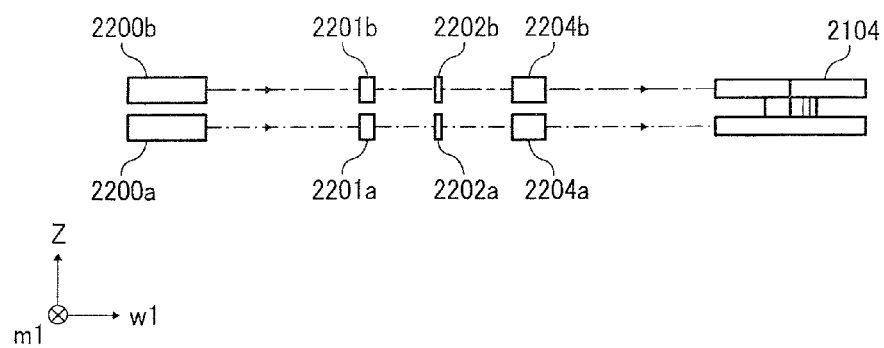
FIG. 3 is a second schematic diagram of the configuration of the optical scanning device.
Figure 4:
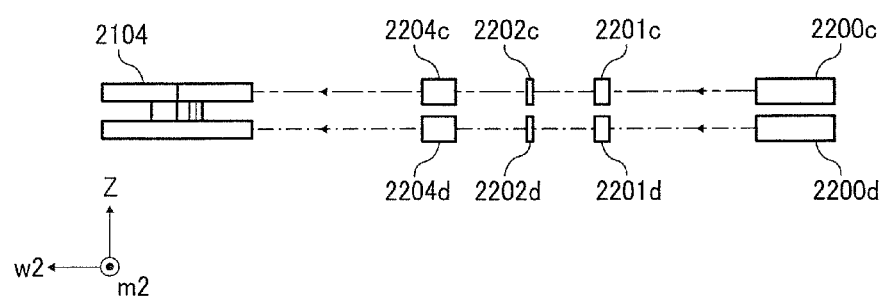
FIG. 4 is a third schematic diagram of the configuration of the optical scanning device.
Figure 5:
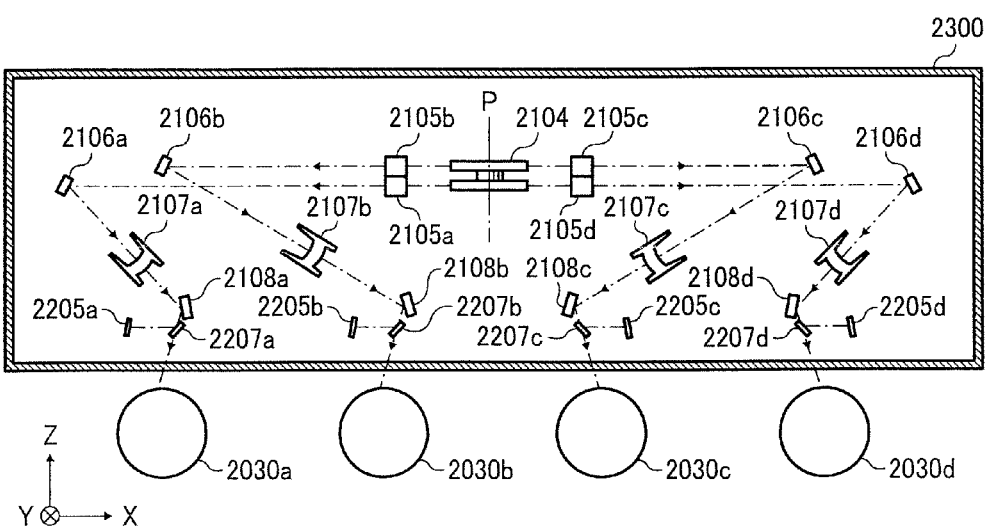
FIG. 5 is a fourth schematic diagram of the configuration of the optical scanning device.

Exemplary embodiments of the present invention are described in detail below with reference to FIGS. 1 to 40E. FIG. 1 is a schematic diagram of the configuration of a color printer 2000. The color printer 2000 corresponds to an image forming apparatus according to an embodiment of the present invention.

The color printer 2000 is a tandem-type multi-color printer that forms a full-color image by superimposing four colors (black, cyan, magenta, and yellow). The color printer 2000 includes an optical scanning device 2010, four drum-shaped photosensitive elements (2030a, 2030b, 2030c, and 2030d), four cleaning units (2031a, 2031b, 2031c, and 2031d), four charging devices (2032a, 2032b, 2032c, and 2032d), four developing rollers (2033a, 2033b, 2033c, and 2033d), four toner cartridges (2034a, 2034b, 2034c, and 2034d), a transfer belt 2040, a transfer roller 2042, a fixing roller 2050, a paper-feed roller 2054, a pair of registration rollers 2056, a paper-discharge roller 2058, a paper-feed tray 2060, a discharge tray 2070, a communication control device 2080, a toner detector 2245, a printer control device 2090 that totally controls the above units, etc.

It is assumed that, in an XYZ three-dimensional orthogonal coordinate system, the longitudinal direction of each photosensitive element corresponds to the Y-axis direction and the alignment direction of the four photosensitive elements corresponds to the X-axis direction.

The communication control device 2080 controls bidirectional communication that is made with a higher-level device (e.g., a personal computer) via a network or similar.

Each photosensitive element has a surface with a photosensitive layer being formed thereon. This surface of each photosensitive element is a scanned surface. Each photosensitive element is rotated by a rotating mechanism (not shown) in the direction indicated by the arrow in the plane of paper of FIG. 1.

Near the surface of the photosensitive element 2030a are the charging device 2032a, the developing roller 2033a, and the cleaning unit 2031a arranged in the rotating direction of the photosensitive element 2030a.

The photosensitive element 2030a, the charging device 2032a, the developing roller 2033a, the toner cartridge 2034a, and the cleaning unit 2031a together form an image forming station for black images (hereinafter, "K station") and they operate as a unit.

Near the surface of the photosensitive element 2030b are the charging device 2032b, the developing roller 2033b, and the cleaning unit 2031b arranged in the rotating direction of the photosensitive element 2030b.

The photosensitive element 2030b, the charging device 2032b, the developing roller 2033b, the toner cartridge 2034b, and the cleaning unit 2031b together form an image forming station for cyan images (hereinafter, "C station") and they operate as a unit.

Near the surface of the photosensitive element 2030c are the charging device 2032c, the developing roller 2033c, and the cleaning unit 2031c arranged in the rotating direction of the photosensitive element 2030c.

The photosensitive element 2030c, the charging device 2032c, the developing roller 2033c, the toner cartridge 2034c, and the cleaning unit 2031c together form an image forming station for magenta images (hereinafter, "M station") and they operate as a unit.

Near the surface of the photosensitive element 2030d are the charging device 2032d, the developing roller 2033d, and the cleaning unit 2031d arranged in the rotating direction of the photosensitive element 2030d.

The photosensitive element 2030d, the charging device 2032d, the developing roller 2033d, the toner cartridge 2034d, and the cleaning unit 2031d together form an image forming station for yellow images (hereinafter, "Y station") and they operate as a unit.

Each charging device evenly charges the surface of the corresponding photosensitive element.

The optical scanning device 2010 illuminates the charged surface of the corresponding photosensitive element with a beam of light that is modulated for the corresponding color in accordance with multi-color image data (containing black image data, cyan image data, magenta image data, or yellow image data) that has been received from the higher-level device. Thus, part of the surface of the photosensitive element irradiated by the light is discharged and a latent image is formed on the surface of each photosensitive element in accordance with the image data. The formed latent image moves toward the corresponding developing roller by rotation of the photosensitive element. The configuration of the optical scanning device 2010 will be described later.

The toner cartridge 2034a accommodates black toner and the black toner is supplied to the developing roller 2033a, The toner cartridge 2034b accommodates cyan toner and the cyan toner is supplied to the developing roller 2033b. The toner cartridge 2034c accommodates magenta toner and the magenta toner is supplied to the developing roller 2033c. The toner cartridge 2034d accommodates yellow toner and the yellow toner is supplied to the developing roller 2033d.

Each developing roller rotates to receive the corresponding toner from the corresponding toner cartridge so that the surface is covered with the toner evenly and thinly. When the toner on the surface of each developing roller comes into contact with the corresponding photosensitive element, the toner is attached to only the part of the surface irradiated with the light. Using each developing roller, toner is attached to the latent image that is formed on the surface of the corresponding photosensitive element, and thus a visible image is formed. The image attached with toner (toner image) is then conveyed toward the transfer belt 2040 by rotation of the photosensitive element.

Each of the yellow toner image, the magenta toner image, the cyan toner image, and the black toner image is sequentially transferred onto the transfer belt 2040 at a predetermined point of time in a superimposed manner and thus a color image is formed. The direction in which the toner image is conveyed on the transfer belt 2040 is called "sub direction" and the direction perpendicular to the sub direction (herein, the Y-axis direction) is called "main direction".

The paper-feed tray 2060 accommodates recording sheets. The paper-feed roller 2054 is arranged near the paper-feed tray 2060. The paper-feed roller 2054 picks up recording sheets one by one from the paper-feed tray 2060 and conveys the recording sheet to the registration rollers 2056. The registration rollers 2056 convey the recording sheet to between the transfer belt 2040 and the transfer roller 2042 at a predetermined point of time. The color image is then transferred from the transfer belt 2040 onto the recording sheet. The recording sheet with the color image is conveyed to the fixing roller 2050.

Heat and pressure is applied to the recording sheet using the fixing roller 2050 and thus the toner is fixed onto the recording sheet. The recording sheet with the toner fixed thereon is conveyed to the discharge tray 2070 via the paper-discharge roller 2058 and the recording sheets are stacked on the discharge tray 2070 one after another.

Each cleaning device removes toner (residual toner) from the surface of the corresponding photosensitive element. After the residual toner is removed from the surface of the photosensitive element, the surface with no residual toner rotates back to the position facing to the corresponding charging device.

The toner detector 2245 is at the −X side of the transfer belt 2040 and outputs a signal that contains the position and the toner density of a toner pattern that is a detection pattern formed on the transfer belt 2040. The toner detector 2245 will be described in detail later.

The configuration of the optical scanning device 2010 is described below.

As shown in FIGS. 2 to 5, the optical scanning device 2010 includes, for example, four light sources (2200a, 2200b, 2200c, and 2200d), four coupling lenses (2201a, 2201b, 2201c, and 2201d), four aperture plates (2202a, 2202b, 2202c, and 2202d), four cylindrical lenses (2204a, 2204b, 2204c, and 2204d), a polygon mirror 2104, four fθ lenses (2105a, 2105b, 2105c, and 2105d), eight reflecting mirrors (2106a, 2106b, 2106c, 2106d, 2108a, 2108b, 2108c, and 2108d), four toroidal lenses (2107a, 2107b, 2107c, and 2107d), four optical detection sensors (2205a, 2205b, 2205c, and 2205d), four optical detecting mirrors (2207a, 2207b, 2207c, and 2207d), and a scanning control device (not shown). These components are arranged at predetermined positions of an optical-system housing 2300 (not shown in FIGS. 2 to 4, see FIG. 5).

Hereinafter, the direction corresponding to the main-scanning direction is called "main-scanning corresponding direction" and the direction corresponding to the sub-scanning direction is called "sub-scanning corresponding direction".

Moreover, herein, the direction along the optical axis of the coupling lenses 2201a and 2201b is called "direction w1"; the main-scanning corresponding direction at the light sources 2200a and 2200b is called "direction m1". Moreover, the direction along the optical axis of the coupling lenses 2201c and 2201d is called "direction w2"; the main-scanning corresponding direction at the light sources 2200c and 2200d is called "direction m2". Both the sub-scanning corresponding direction at the light sources 2200a and 2200b and the sub-scanning corresponding direction at the light sources 2200c and 2200d are the same direction as the Z-axis direction.

The light sources 2200b and 2200c are away from each other in the X-axis direction. The light source 2200a is at the -Z side of the light source 2200b. The light source 2200d is at the -Z side of the light source 2200c.

The coupling lens 2201a is on the optical path of the beam of light emitted from the light source 2200a and converts the beam of light into a substantially parallel light beam.

The coupling lens 2201b is on the optical path of the beam of light emitted from the light source 2200b and converts the beam of light into a substantially parallel light beam.

The coupling lens 2201c is on the optical path of the beam of light emitted from the light source 2200c and converts the beam of light into a substantially parallel light beam.

The coupling lens 2201d is on the optical path of the beam of light emitted from the light source 2200d and converts the beam of light into a substantially parallel light beam.

The aperture plate 2202a has an aperture and shapes the beam of light passed through the coupling lens 2201a.

The aperture plate 2202b has an aperture and shapes the beam of light passed through the coupling lens 2201b.

The aperture plate 2202c has an aperture and shapes the beam of light passed through the coupling lens 2201c.

The aperture plate 2202d has an aperture and shapes the beam of light passed through the coupling lens 2201d.

The cylindrical lens 2204a focuses the beam of light after passing through the aperture of the aperture plate 2202a, at a position near a deflecting/reflecting surface of the polygon mirror 2104 in the Z-axis direction.

The cylindrical lens 2204b focuses the beam of light after passing through the aperture of the aperture plate 2202b, at a position near the deflecting/reflecting surface of the polygon mirror 2104 in the Z-axis direction.

The cylindrical lens 2204c focuses the beam of light after passing through the aperture of the aperture plate 2202c, at a position near the deflecting/reflecting surface of the polygon mirror 2104 in the Z-axis direction.

The cylindrical lens 2204d focuses the beam of light after passing through the aperture of the aperture plate 2202d, at a position near the deflecting/reflecting surface of the polygon mirror 2104 in the Z-axis direction.

The polygon mirror 2104 has an upper layer and a lower layer each having four-faceted mirror. Each mirror forms deflecting/reflecting surfaces. The four-faceted mirror of the lower layer is positioned to deflect the beams of light coming from the cylindrical lenses 2204a and 2204d; the four-faceted mirrors of the upper layer is positioned to deflect the beams of light coming from the cylindrical lenses 2204b and 2204c. The four-faceted mirrors of the lower layer and the upper layer rotate in such a manner that the phase of the four-faceted mirror of the lower layer is shifted 45° from the phase of the four-faceted mirror of the upper layer. Therefore, writing/scanning using the lower layer and writing/scanning using the upper layer are performed alternatively.

The beams of light coming from the cylindrical lenses 2204a and 2204b are deflected toward the -X side of the polygon mirror 2104; the beams of light coming from the cylindrical lenses 2204c and 2204d are deflected toward the +X side of the polygon mirror 2104.

Each fθ lens has a noncircular surface that has a power to cause the light spot to move in the main-scanning direction at a constant speed on the surface of the corresponding photosensitive element by rotation of the polygon mirror 2104.

The fθ lenses 2105a and 2105b are at the -X side of the polygon mirror 2104; the fθ lenses 2105c and 2105d are at the +X side of the polygon mirror 2104.

The fθ lenses 2105a and 2105b are piled on each other in the Z-axis direction so that the fθ lens 2105a faces to the four-faceted mirror of the lower layer and the fθ lens 2105b faces to the four-faceted mirror of the upper layer. The fθ lenses 2105c and 2105d are piled on each other in the Z-axis direction so that the fθ lens 2105c faces to the four-faceted mirror of the upper layer and the fθ lens 2105d faces to the four-faceted mirror of the lower layer.

After the beam of light coming from the cylindrical lens 2204a is deflected by the polygon mirror 2104, the deflected beam of light passes through the fθ lens 2105a, the reflecting mirror 2106a, the toroidal lens 2107a, and the reflecting mirror 2108a and then irradiates the photosensitive element 2030a, and thus a light spot is formed. The light spot moves in the longitudinal direction of the photosensitive element 2030a by rotation of the polygon mirror 2104. That is, the light spot scans the photosensitive element 2030a. The moving direction of the light spot is the "main-scanning direction" at the photosensitive element 2030a; and the rotating direction of the photosensitive element 2030a is the "sub-scanning direction" at the photosensitive element 2030a.

After the beam of light coming from the cylindrical lens 2204b is deflected by the polygon mirror 2104, the deflected beam of light passes through the fθ lens 2105b, the reflecting mirror 2106b, the toroidal lens 2107b, and the reflecting mirror 2108b and then irradiates the photosensitive element 2030b, and thus a light spot is formed. The light spot moves in the longitudinal direction of the photosensitive element 2030b by rotation of the polygon mirror 2104. That is, the light spot scans the photosensitive element 2030b. The moving direction of the light spot is the "main-scanning direction" at the photosensitive element 2030b; and the rotating direction of the photosensitive element 2030b is the "sub-scanning direction" at the photosensitive element 2030b.

After the beam of light coming from the cylindrical lens 2204c is deflected by the polygon mirror 2104, the deflected beam of light passes through the fθ lens 2105c, the reflecting mirror 2106c, the toroidal lens 2107c, and the reflecting mirror 2108c and then irradiates the photosensitive element 2030c, and thus a light spot is formed. The light spot moves in the longitudinal direction of the photosensitive element 2030c by rotation of the polygon mirror 2104. That is, the light spot scans the photosensitive element 2030c. The moving direction of the light spot is the "main-scanning direction" at the photosensitive element 2030c; and the rotating direction of the photosensitive element 2030c is the "sub-scanning direction" at the photosensitive element 2030c.

After the beam of light coming from the cylindrical lens 2204d is deflected by the polygon mirror 2104, the deflected beam of light passes through the fθ lens 2105d, the reflecting mirror 2106d, the toroidal lens 2107d, and the reflecting mirror 2108d and then irradiates the photosensitive element 2030d, and thus a light spot is formed. The light spot moves in the longitudinal direction of the photosensitive element 2030d by rotation of the polygon mirror 2104. That is, the light spot scans the photosensitive element 2030d. The moving direction of the light spot is the "main-scanning direction" at the photosensitive element 2030d; and the rotating direction of the photosensitive element 2030d is the "sub-scanning direction" at the photosensitive element 2030d.

It is noted that a scanned area on each photosensitive element in the main-scanning direction to which the image data is written is called "effective scanned area" or "image formed area".

The reflecting mirrors are arranged so that the lengths of the optical pathes between the polygon mirror 2104 and the different photosensitive elements are set equal to each other and the positions of incidences and the angles of incidences of the beams of light are set identical between different photosensitive elements.

Moreover, the cylindrical lens and the corresponding toroidal lens together form an optical face tangle error correcting system that establishes the conjugate relation between the point of deflection and the surface of the corresponding photosensitive element in the sub-scanning direction.

The optical system that is arranged on the optical path between the polygon mirror 2104 and each photosensitive element is also called "optical scanning system". In the present embodiment, the fθ lens 2105a, the toroidal lens 2107a, and the reflecting mirrors (2106a and 2108a) together form the optical scanning system for the K station. The fθ lens 2105b, the toroidal lens 2107b, and the reflecting mirrors (2106b and 2108b) together form the optical scanning system for the C station. The fθ lens 2105c, the toroidal lens 2107c, and the reflecting mirrors (2106c and 2108c) together form the optical scanning system for the M station. The fθ lens 2105d, the toroidal lens 2107d, and the reflecting mirrors (2106d and 2108d) together form the optical scanning system for the Y station.

The optical detection sensor 2205a receives, via the optical detecting mirror 2207a before the start of writing, part of the beam of light that has been deflected by the polygon mirror 2104 and then output from the scanning optical system for the K station.

The optical detection sensor 2205b receives, via the optical detecting mirror 2207b before the start of writing, part of the beam of light that has been deflected by the polygon mirror 2104 and then output from the scanning optical system for the C station.

The optical detection sensor 2205c receives, via the optical detecting mirror 2207c before the start of writing, part of the beam of light that has been deflected by the polygon mirror 2104 and then output from the scanning optical system for the M station.

The optical detection sensor 2205d receives, via the optical detecting mirror 2207d before the start of writing, part of the beam of light that has been deflected by the polygon mirror 2104 and then output from the scanning optical system for the Y station.

Each optical detection sensor outputs a signal in accordance with the intensity of received light (photoelectric conversion signal).

The scanning control device calculates, in accordance with the signal output from each optical detection sensor, a start time of scanning the corresponding photosensitive element.

The toner detector 2245 is described below.

Figure 6:
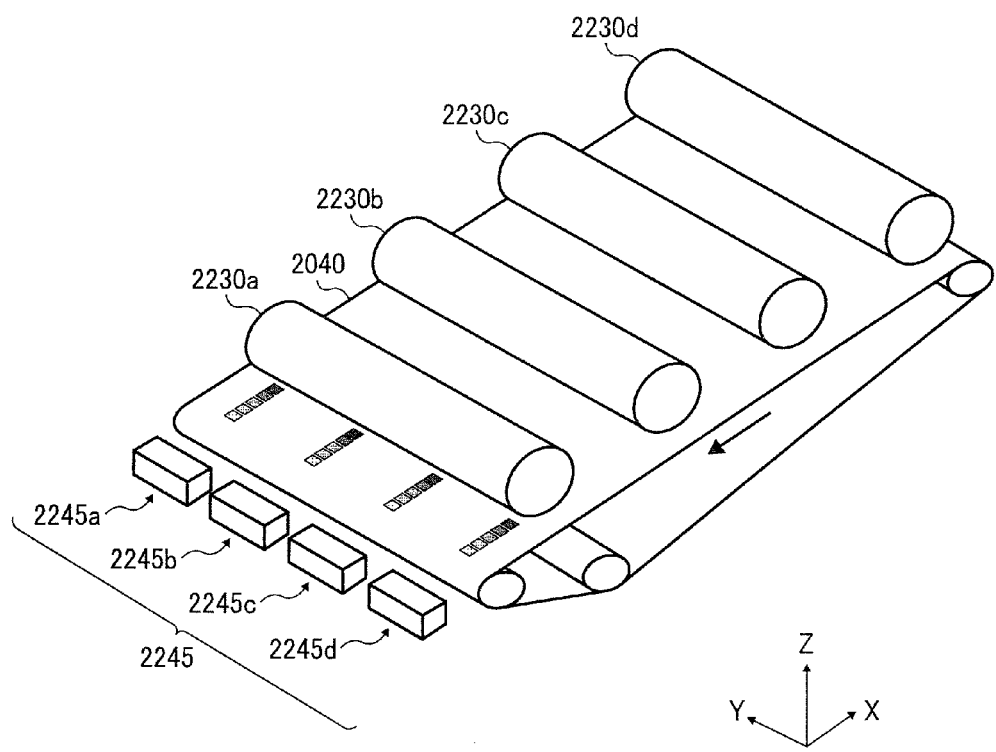
FIG. 6 is a perspective view of the toner detector shown in FIG. 1.

The toner detector 2245 includes, as shown in FIG. 6 for example, four reflective optical sensors (2245a, 2245b, 2245c, and 2245d).

The reflective optical sensor 2245a is positioned to face a portion of the transfer belt 2040 near the +Y-side edge thereof; the reflective optical sensor 2245d is positioned to face a portion of the transfer belt near the −Y-side edge thereof. The reflective optical sensor 2245b is at the −Y side of the reflective optical sensor 2245a; the reflective optical sensor 2245c is at the +Y side of the reflective optical sensor 2245d. The reflective optical sensors 2245b and 2245c are arranged so that the intervals of the reflective optical sensors are set substantially equal in the Y-axis direction.

Figure 7:
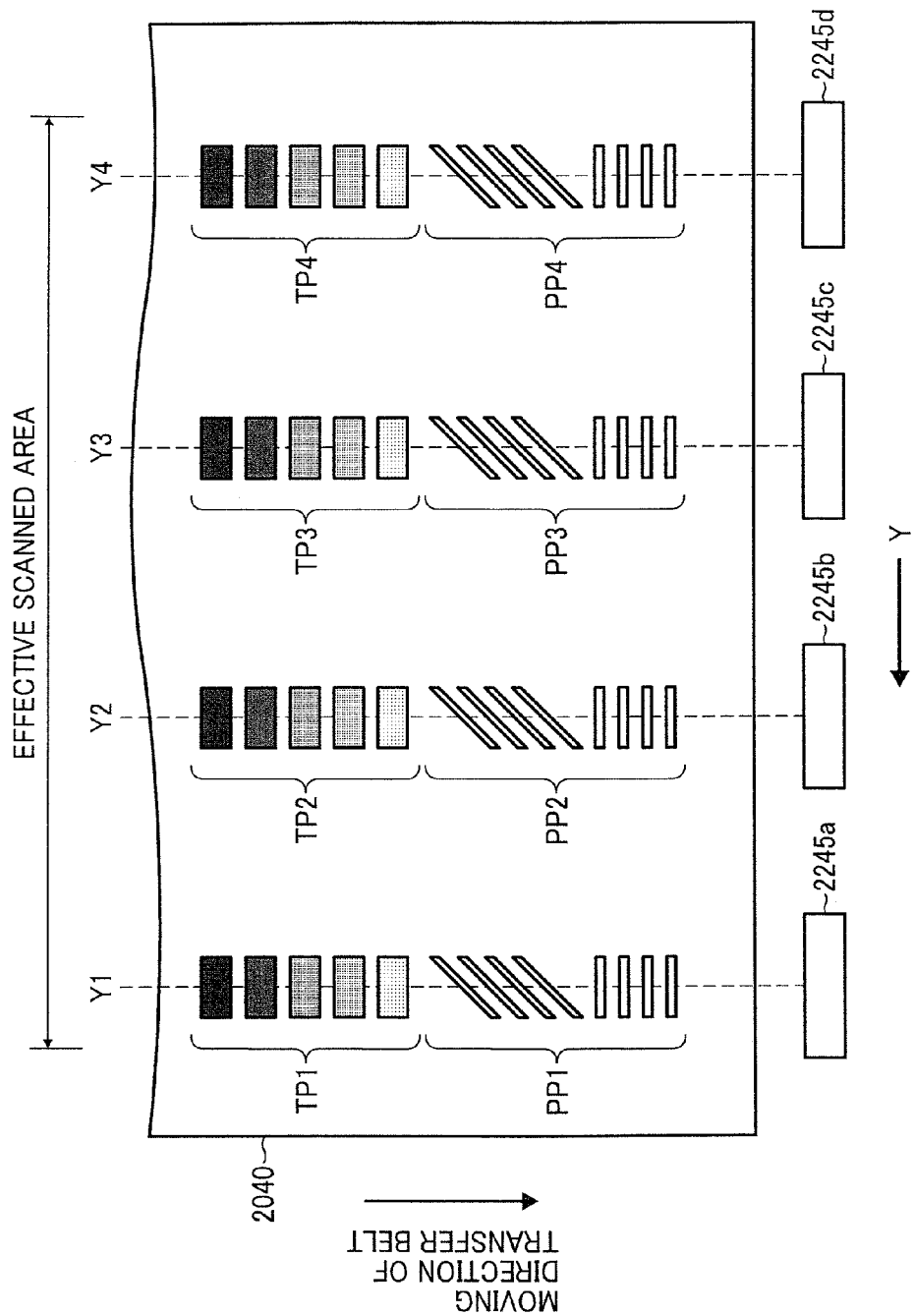
FIG. 7 is a schematic diagram of arrangement of reflective optical sensors.

As shown in FIG. 7 for example, in the Y-axis direction, the center position of the reflective optical sensor 2245a is Y1; the center position of the reflective optical sensor 2245b is Y2; the center position of the reflective optical sensor 2245c is Y3; and the center position of the reflective optical sensor 2245d is Y4.

The toner pattern facing to the reflective optical sensor 2245a includes toner patterns PP1 and TP1; the toner pattern facing to the reflective optical sensor 2245b includes toner patterns PP2 and TP2; the toner pattern facing to the reflective optical sensor 2245c includes toner patterns PP3 and TP3; the toner pattern facing to the reflective optical sensor 2245d includes toner patterns PP4 and TP4.

The toner patterns PP1, PP2, PP3, and PP4 are position detection patterns; the toner patterns TP1, TP2, TP3, and TP4 are density detection patterns.

The position detection patterns PP1, PP2, PP3, and PP4 have the same structure. If there is no need to identify the individual position detection patterns, they are also called, herein, "position detection pattern PP" collectively.

Figure 8:
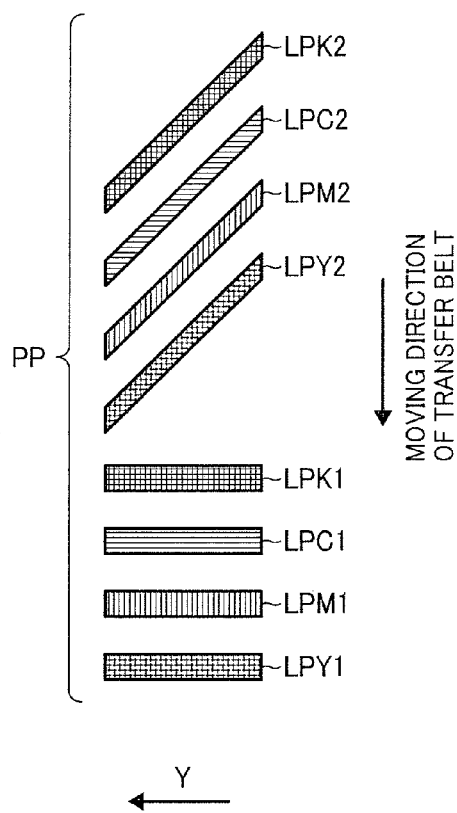
FIG. 8 is a schematic diagram of a position detection pattern.

The position detection pattern PP includes, as shown in FIG. 8, four line patterns (LPY1, LPM1, LPC1, and LPK1) each parallel to the main direction (Y-axis direction) and four line patterns (LPY2, LPM2, LPC2, and LPK2) each makes a certain angle with the main direction.

The line patterns LPY1 and LPY2 are formed with yellow toner and together make a pair; the line patterns LPM1 and LPM2 are formed with magenta toner and together make a pair; the line patterns LPC1 and LPC2 are formed with cyan toner and together make a pair; the line patterns LPK1 and LPK2 are formed with black toner and together make a pair.

Each pair of the line patterns is arranged so that the interval between the two line patterns is set to a predetermined value in the moving direction of the transfer belt 2040.

The density detection pattern TP1 is formed with yellow toner; the density detection pattern TP2 is formed with magenta toner. The density detection pattern TP3 is formed with cyan toner; the density detection pattern TP4 is formed with black toner. If there is no need to identify the individual density detection patterns, they are also called, herein, "density detection pattern TP" collectively.

Figure 9:
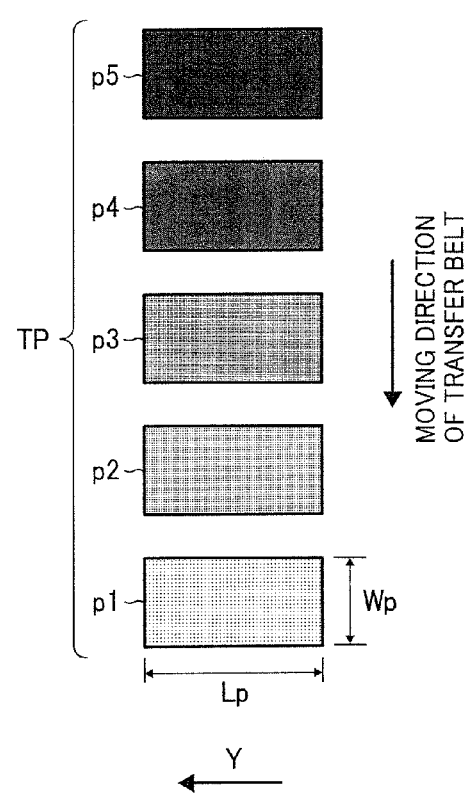
FIG. 9 is a schematic diagram of a density detection pattern.

The density detection pattern TP includes, as shown in FIG. 9 for example, five quadrangle patterns (p1 to p5, hereinafter, "rectangular patterns"). The rectangular patterns aligned in a row along the moving direction of the transfer belt 2040. The rectangular patterns have different toner densities when comparing the whole. In this example, the rectangular pattern p1 has the lowest toner density, the rectangular pattern p2 has the second lowest, the rectangular pattern p3 has the third lowest, the rectangular pattern p4 has the fourth lowest, and the rectangular pattern p5 has the highest.

The length of each rectangular pattern is Lp in the Y-axis direction, and the length of the transfer belt 2040 is Wp in the moving direction. In this example, Lp=1.0 mm.

The gradation by the toner density is adjustable by means of power adjustment of the beam of light emitted from the light source, duty cycle adjustment of the driving pulse that is supplied to the light source, and developing bias adjustment.

Moreover, if there is no need to distinguish between the position detection patterns and the density detection patterns, they are called, herein, "toner pattern" collectively.

When the position detecting process and the density detecting process are performed using the toner detector 2245, an instruction is sent from the printer control device 2090 to the scanning control device to form the position detection pattern and the density detection pattern.

Figure 10:
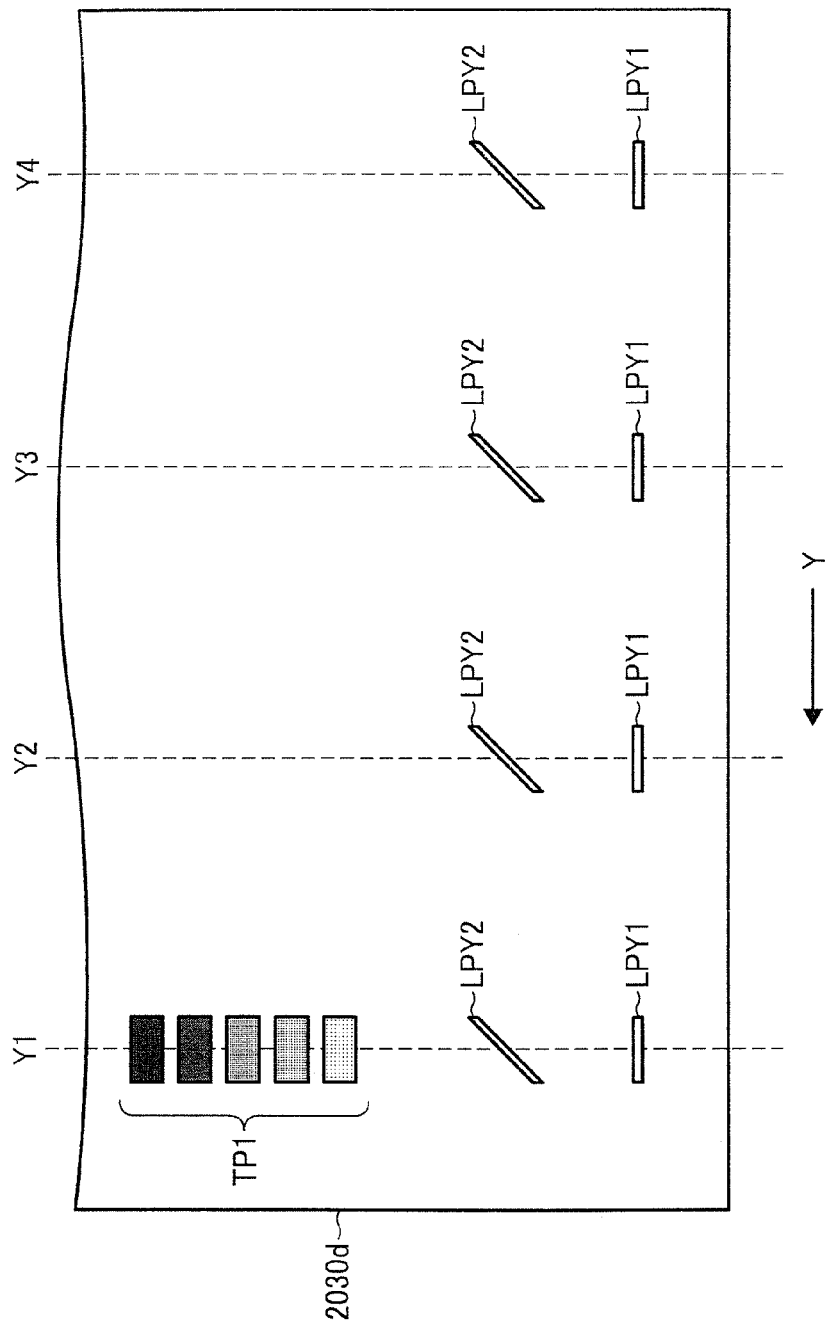
FIG. 10 is a schematic diagram that explains toner-pattern formation by a Y station.

The scanning control device causes the Y station to form the line patterns LPY1 and LPY2 at the positions Y1, Y2, Y3, and Y4 on the photosensitive element 2030d and the density detection pattern TP1 at the position Y1 (see FIG. 10).

Figure 11:
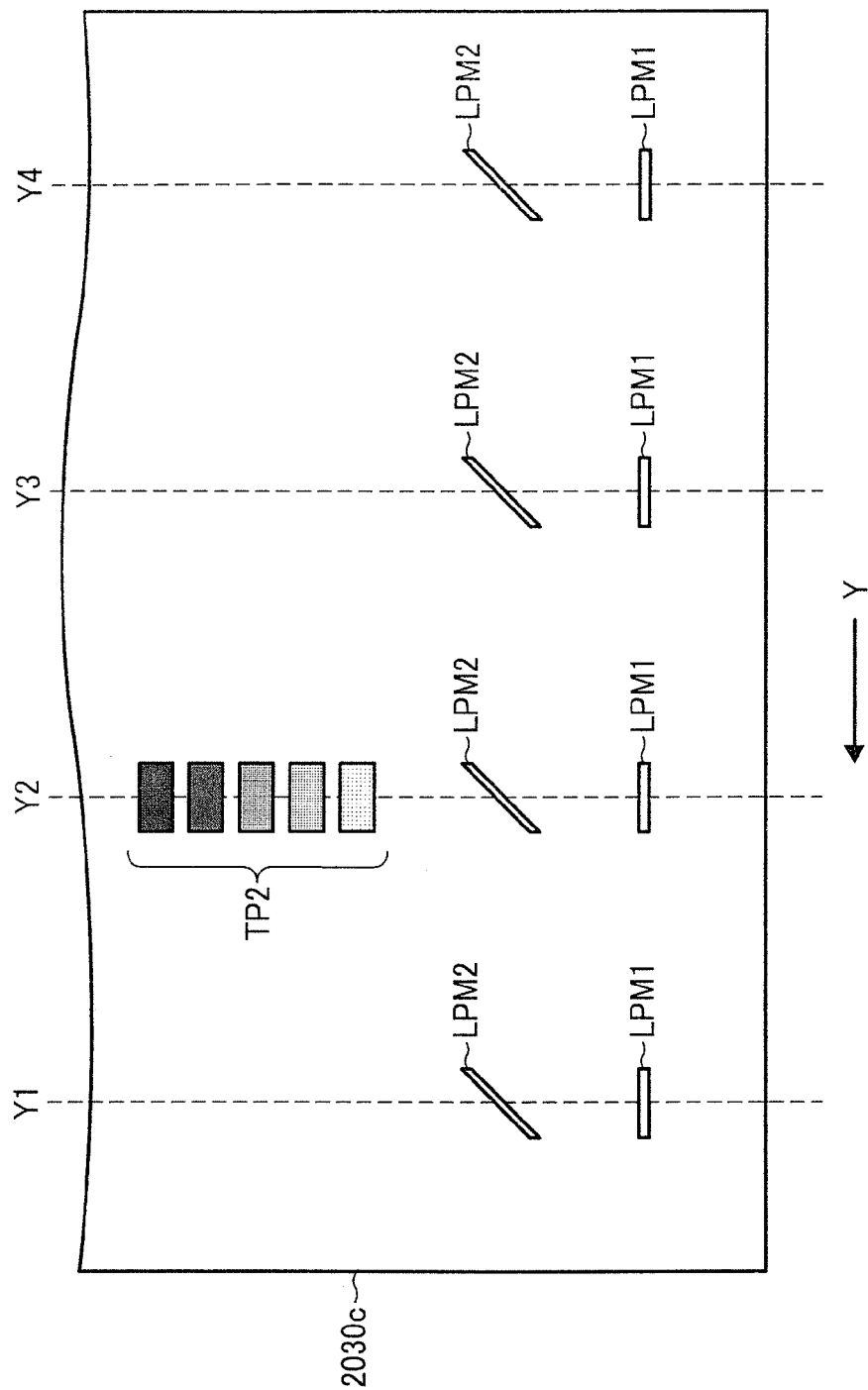
FIG. 11 is a schematic diagram that explains toner-pattern formation by an M station.

The scanning control device causes the M station to form the line patterns LPM1 and LPM2 at the positions Y1, Y2, Y3, and Y4 on the photosensitive element 2030c and the density detection pattern TP2 at the position Y2 (see FIG. 11).

Figure 12:
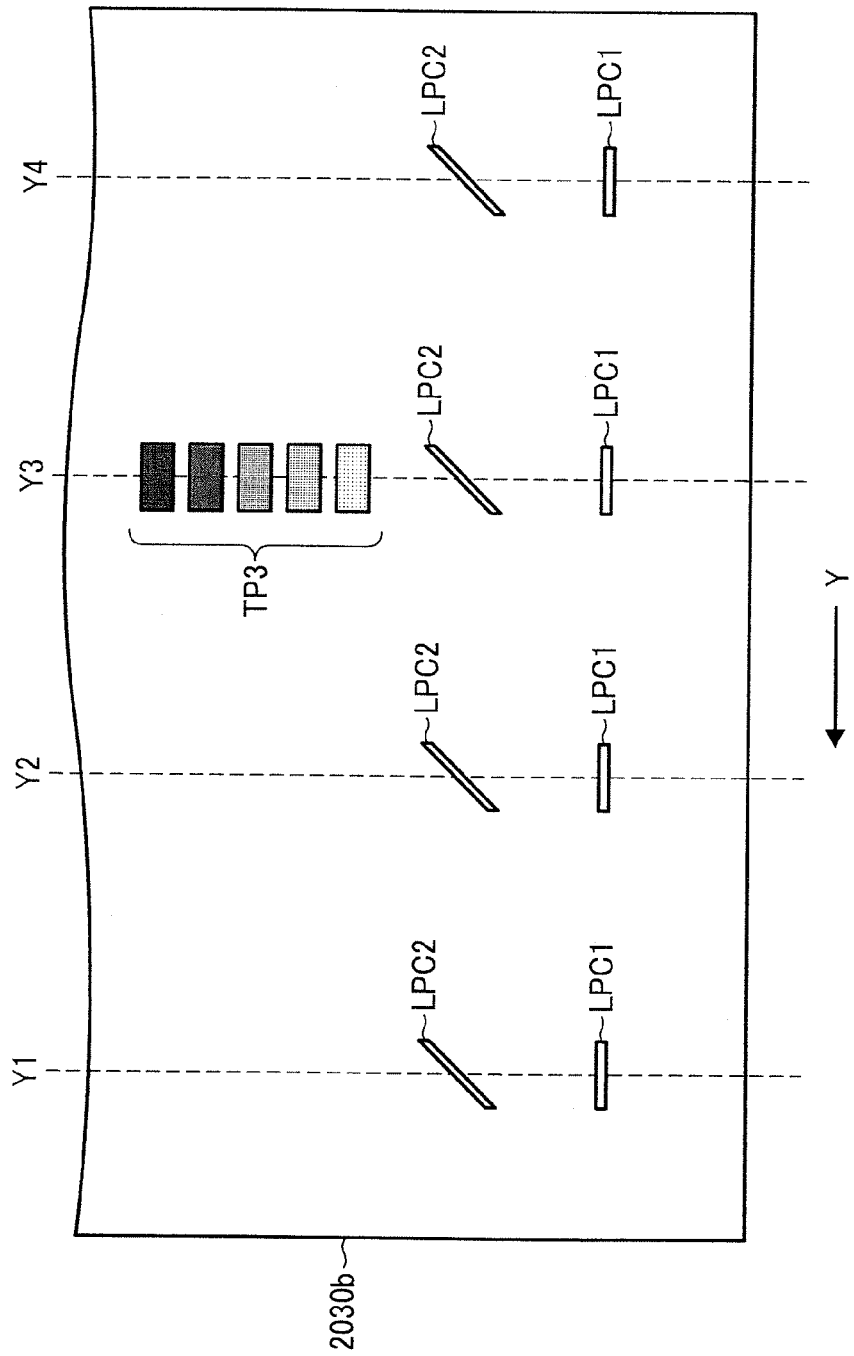
FIG. 12 is a schematic diagram that explains toner-pattern formation by a C station.

The scanning control device causes the C station to form the line patterns LPC1 and LPC2 at the positions Y1, Y2, Y3, and Y4 on the photosensitive element 2030b and the density detection pattern TP3 at the position Y3 (see FIG. 12).

Figure 13:
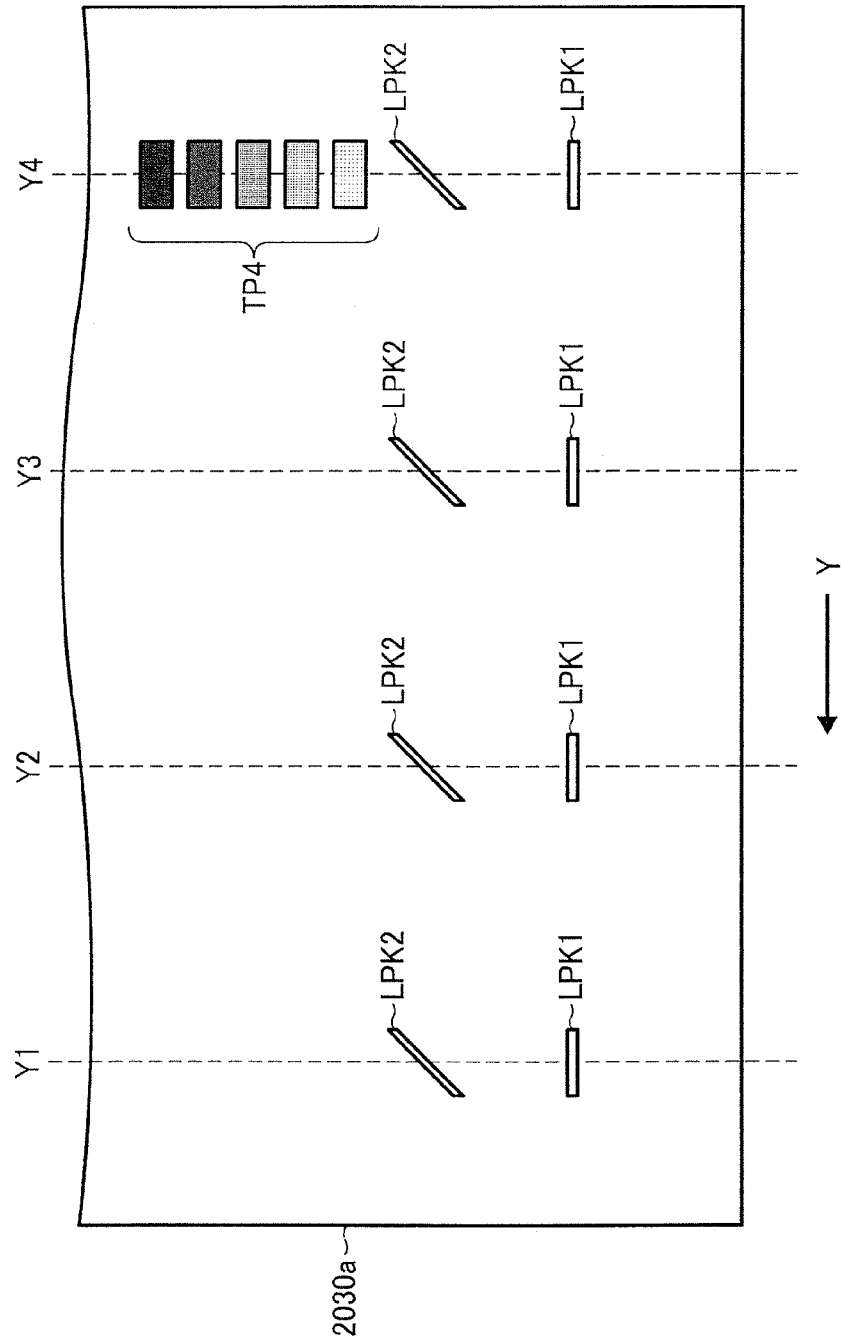
FIG. 13 is a schematic diagram that explains toner-pattern formation by a K station.

The scanning control device causes the K station to form the line patterns LPK1 and LPK2 at the positions Y1, Y2, Y3, and Y4 on the photosensitive element 2030a and the density detection pattern TP4 at the position Y4 (see FIG. 13).

The line patterns LPY1 and LPY2 and the density detection pattern TP1 formed by the Y station are transferred to the transfer belt 2040 at a predetermined point of time.

The line patterns LPM1 and LPM2 and the density detection pattern TP2 formed by the M station are transferred to the transfer belt 2040 at a predetermined point of time.

The line patterns LPC1 and LPC2 and the density detection pattern TP3 formed by the C station are transferred to the transfer belt 2040 at a predetermined point of time.

The line patterns LPK1 and LPK2 and the density detection pattern TP4 formed by the K station are transferred to the transfer belt 2040 at a predetermined point of time.

Figure 14:
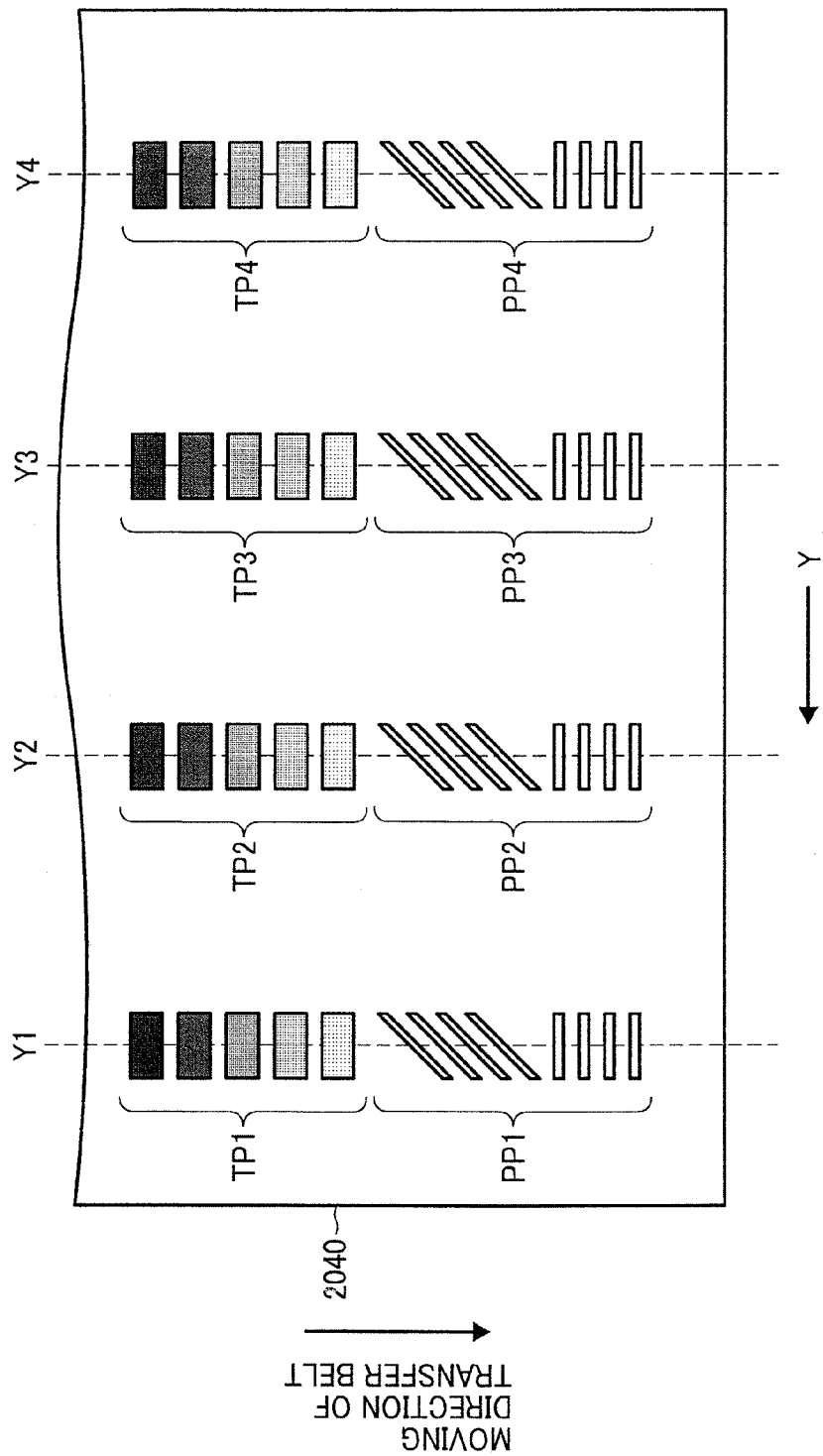
FIG. 14 is a schematic diagram of the toner pattern that has been transferred onto a transfer belt.

As a result, the position detection patterns and the density detection patterns are formed at the positions Y1, Y2, Y3, and Y4 on the transfer belt 2040 (see FIG. 14).

The four reflective optical sensors (2245a, 2245b, 2245c, and 2245d) have the same configuration. Therefore, the configuration of the reflective optical sensor 2245a is described below and the configuration of the other reflective optical sensors will not described herein.

Figure 15:
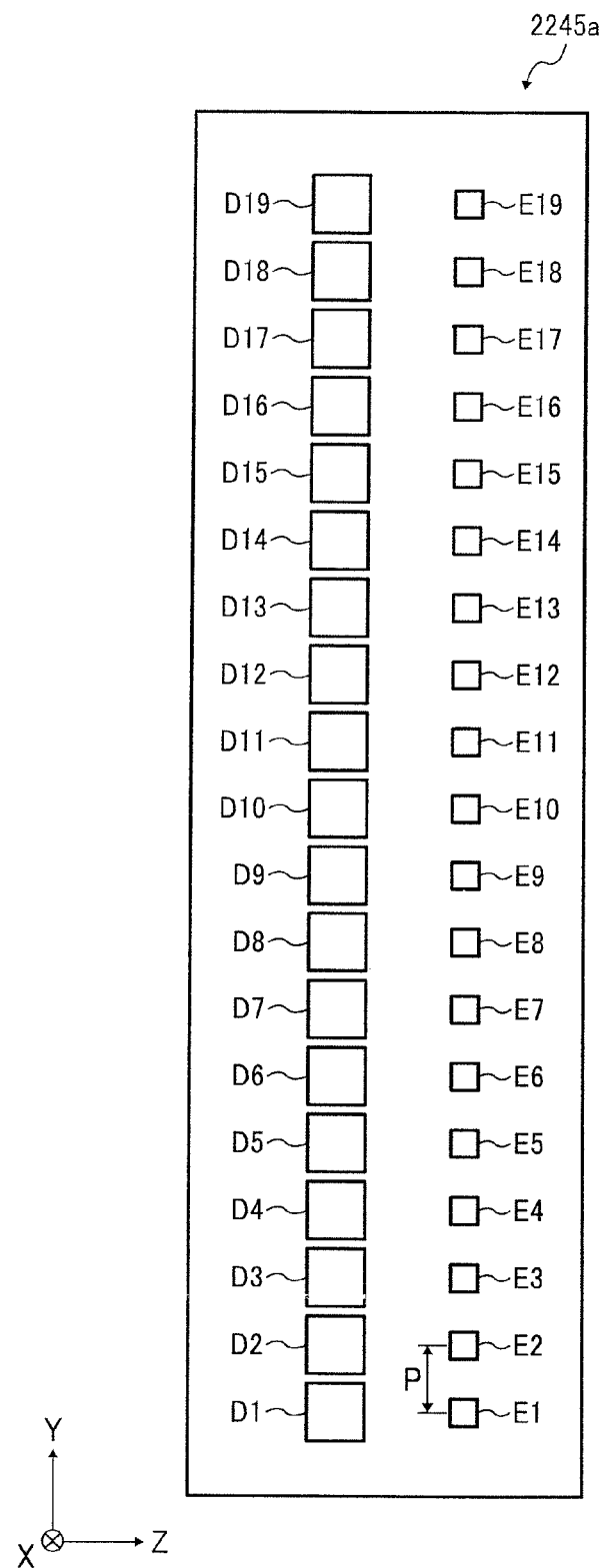
FIG. 15 is a first schematic diagram of the reflective optical sensor.
Figure 16:
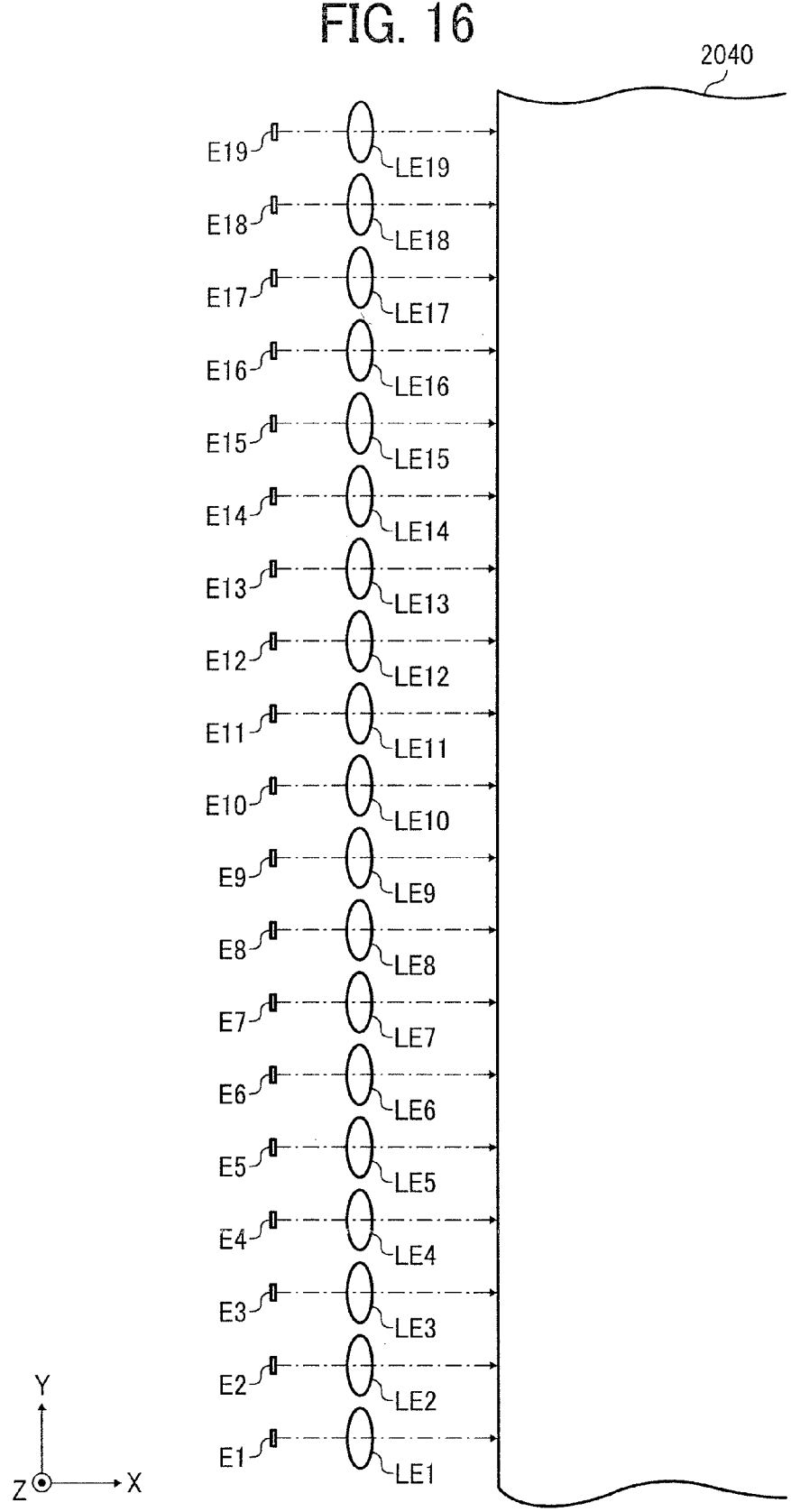
FIG. 16 is a second schematic diagram of the reflective optical sensor.

The reflective optical sensor 2245a includes, as shown in FIGS. 15 and 16 for example, a light-emitting system that includes 19 light-emitting elements (E1 to E19); a lighting optical system that includes 19 lighting collective lenses (LE1 to LE19); a light-receiving system that includes 19 light-receiving elements (D1 to D19); a processing device (not shown), etc.

The 19 light-emitting elements (E1 to E19) are arranged at equal intervals P in the Y-axis direction. Each light-emitting element can be a light emitting diode (LED). The interval P is set to, for example, 0.4 mm. The light-emitting surface of each light-emitting element is parallel to the YZ plane.

The 19 lighting collective lenses (LE1 to LE19) correspond to the 19 light-emitting elements (E1 to E19), respectively. The diameter of each lighting collective lens is, for example, 0.4 mm.

Each lighting collective lens is at +X side of the corresponding light-emitting element and guides the beam of light emitted from the corresponding light-emitting element to the surface of the transfer belt 2040.

Figure 17:
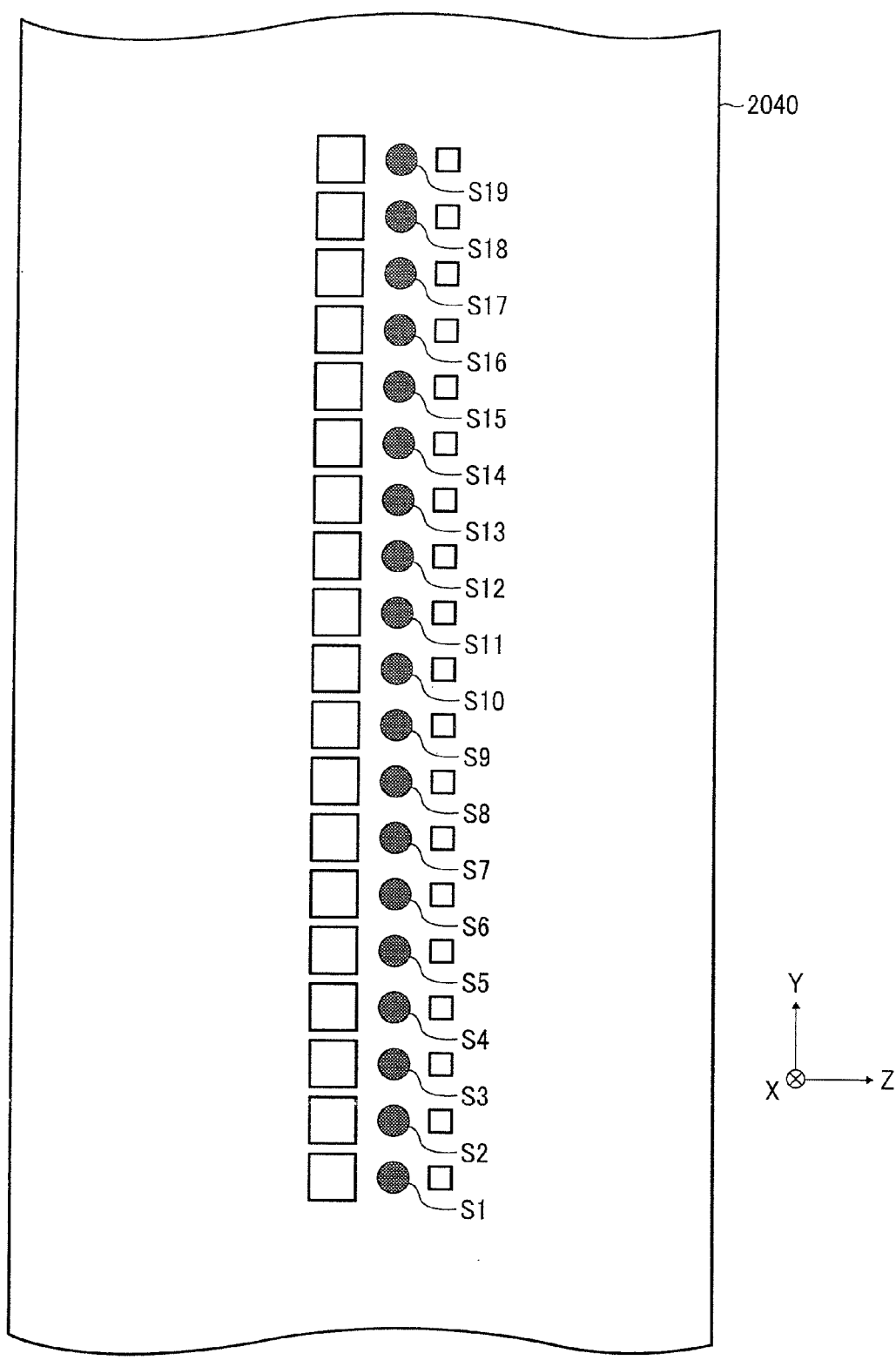
FIG. 17 is a schematic diagram that explains detection light.

To make the description simpler, it is assumed in this example that only if the beam of light emitted from each light-emitting element passes through the corresponding lighting collective lens, the beam of light irradiates the transfer belt 2040 as a beam of detection light (S1 to S19) (see FIG. 17).

The optical axis of each lighting collective lens is parallel to the direction perpendicular to the light-emitting surface of the corresponding light-emitting element (herein, the X-axis direction).

The surface of the transfer belt 2040 is smooth and, therefore, almost all the detection light is reflected specularly.

The diameter of the spot of the detection light formed on the transfer belt 2040 is, for example, 0.2 mm. In contrast, the diameter of the spot of conventional detection light is about from 2 mm to about 3 mm.

Each lighting collective lens can be a spherical lens that can collect light in both the Y-axis direction and the Z-axis direction, a cylindrical lens that has a positive power in the Z-axis direction, or an anamorphic lens that has a first power in the Y-axis direction and a second power in the Z-axis direction in which the first power is different from the second power.

Referring back to FIG. 15, the light-receiving elements (D1 to D19) correspond to the light-emitting elements (E1 to E19), respectively.

Each light-receiving element is at the −Z side of the corresponding light-emitting element and on the optical path of the beam of light specularly reflected from the surface of the transfer belt 2040 after being emitted from the light-emitting element. That is, the arrangement pitch of the 19 light-receiving elements is equal to the arrangement pitch of the 19 light-emitting elements.

Each light-receiving element is configured to receive, when the detection light emitted from the corresponding light-emitting element irradiates the surface of the transfer belt 2040, only specularly reflected light of the detection light.

Each light-receiving element can be a photodiode (PD). Each light-receiving element outputs a signal in accordance with the intensity of received light.

Figure 18:
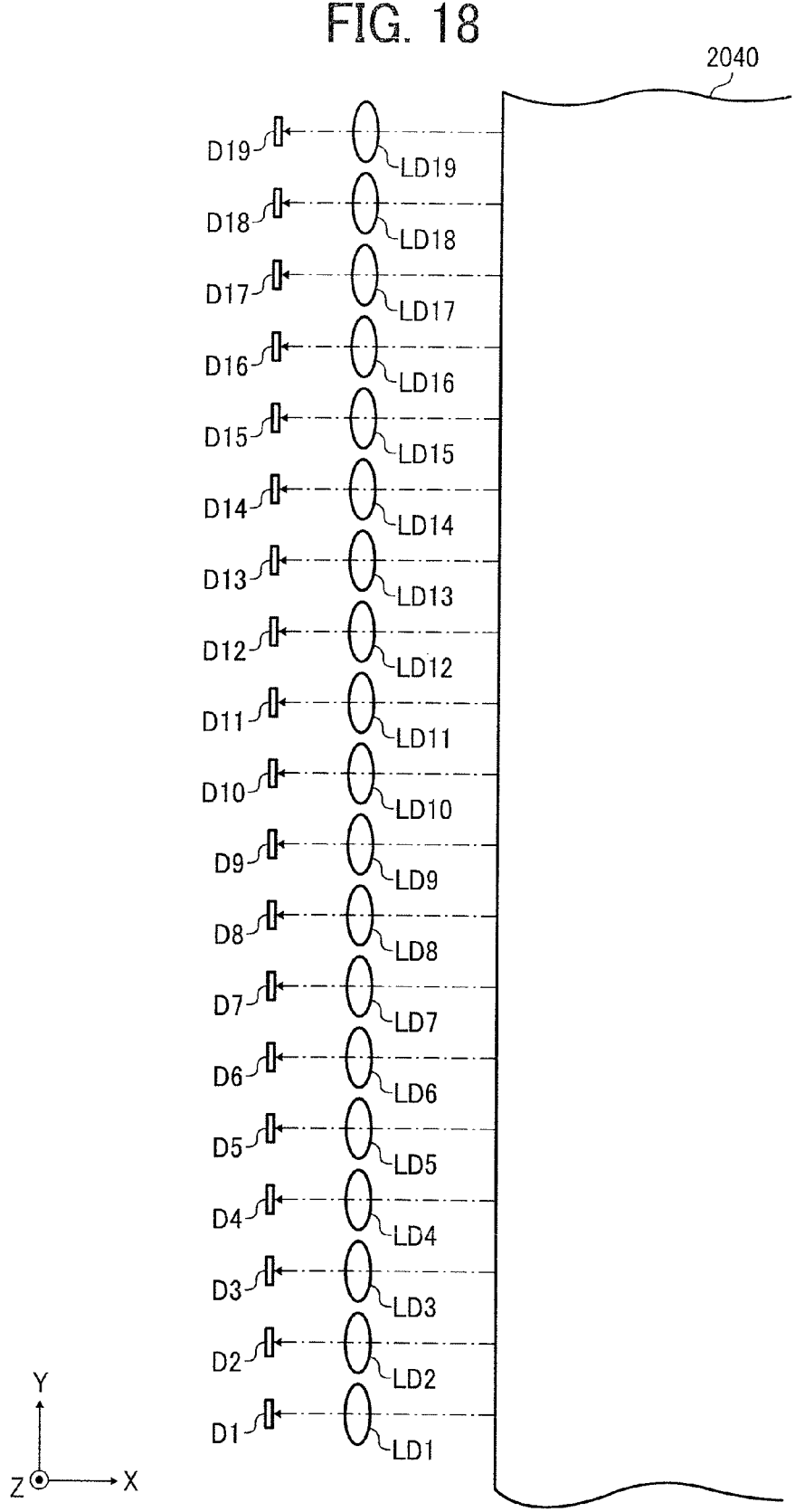
FIG. 18 is a schematic diagram of light receiving collective lenses.

The reflective optical sensor 2245a further includes, as shown in FIG. 18 for example, a light receiving optical system that includes 19 light receiving collective lenses (LD1 to LD19). The light receiving collective lenses (LD1 to LD19) correspond to the 19 light-receiving elements (D1 to D19), respectively. Each light receiving collective lens collects the detection light that has been reflected from the transfer belt 2040 or the toner pattern. In this case, the intensity of light received increases at each light-receiving element. In other words, the sensitivity of detection is improved.

In this example, the optical axis of each light receiving collective lens is parallel to the direction perpendicular to the light-receiving surface of the corresponding light-receiving element (herein, the X-axis direction).

If there is no need to identify the individual light-emitting elements, the light-emitting element is called, herein, "light-emitting element Ei". The lighting collective lens corresponding to the light-emitting element Ei is called "lighting collective lens LEi". The beam of light emitted from the light-emitting element Ei and then passed through the lighting collective lens LEi is called "detection light Si". The light-receiving element corresponding to the light-emitting element Ei is called "light-receiving element Di". The light receiving collective lens corresponding to the light-receiving element Di is called "light receiving collective lens LDi".

The center of the spot of the detection light Si formed on the transfer belt 2040 and the toner pattern is preferably near the middle between the light-emitting element Ei and the light-receiving element Di in the Z-axis direction.

Figure 19:
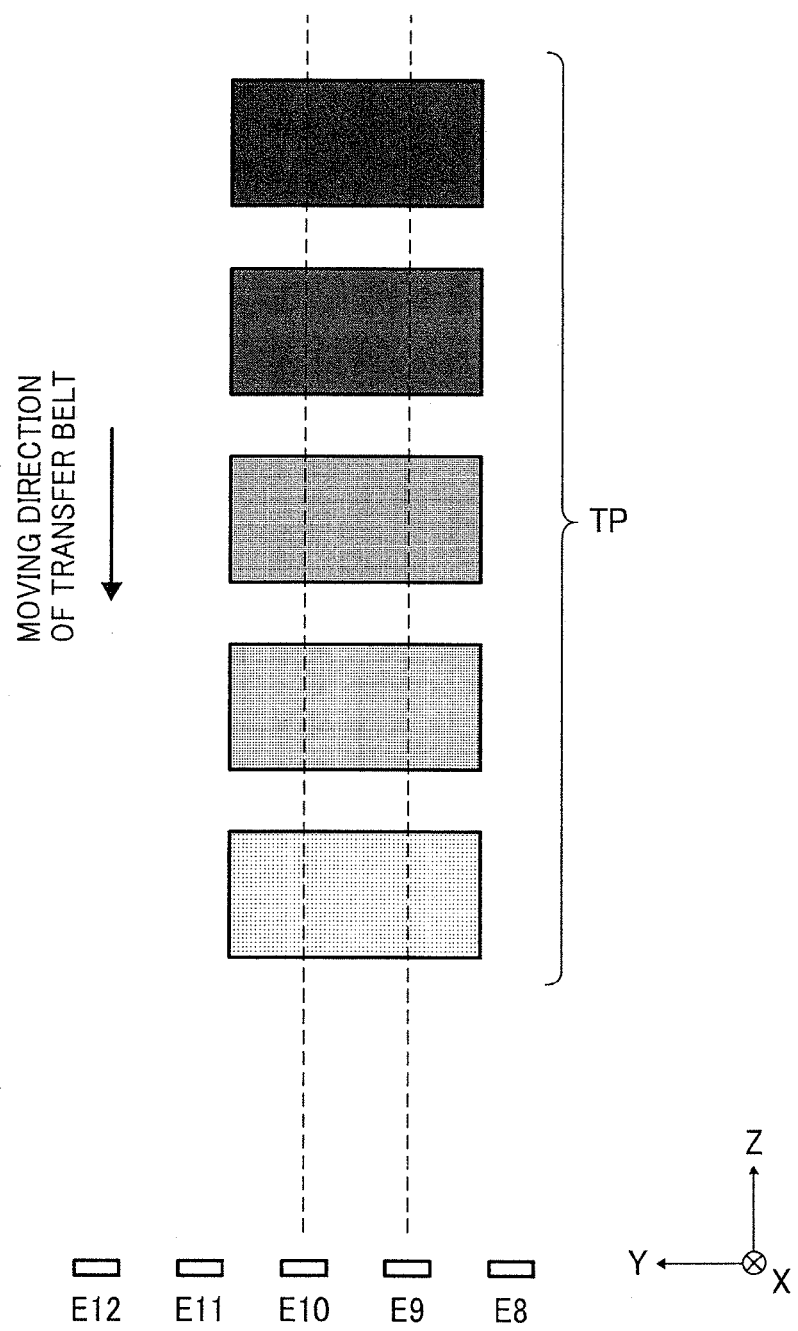
FIG. 19 is a schematic diagram that explains the positional relation between light-receiving elements and the density detection pattern.

For example, to improve the accuracy of toner-density detection, the density detection pattern TP may be formed to face or across over two or more light-emitting elements as shown in FIG. 19.

Figure 20A:
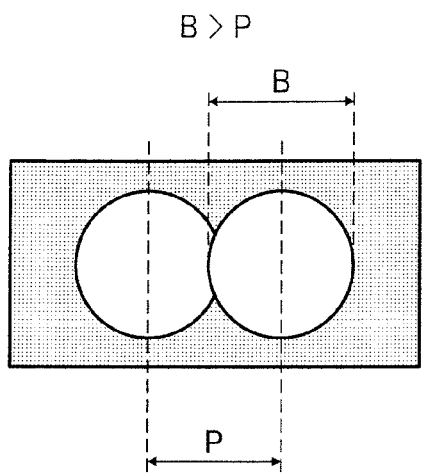
FIGS. 20A and 20B are schematic diagrams that explain the relation between spot size B and arrangement pitch P, where the spot size B is the size of a spot of the detection light formed on the transfer belt, and the arrangement pitch P is the arrangement pitch of the light-receiving elements.
Figure 20B:
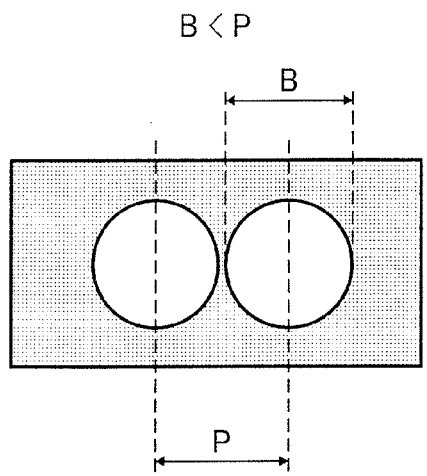

In this case, as shown in FIG. 20A for example, if spot size B, which is the size of each spot of the detection light formed on the transfer belt 2040, is larger than arrangement pitch P, which is the arrangement pitch of the light-emitting elements, the spots of the adjacent light-emitting elements are overlapped with each other and the accuracy of detection decreases when these light-emitting elements emit light at the same time. Therefore, in the present embodiment as shown in FIG. 20B for example, the spot size B of the detection light formed on the transfer belt 2040 is set less than or equal to the arrangement pitch P of the light-emitting elements. In other words, the following inequality (1) is satisfied:

$$B \leq P \tag{1}$$

If the area of the light-emitting surface of the light-emitting element Ei is S and the lateral magnification of the lighting collective lens LEi is m, then the beam diameter of the detection light at the focus position is mS.

Figure 21:
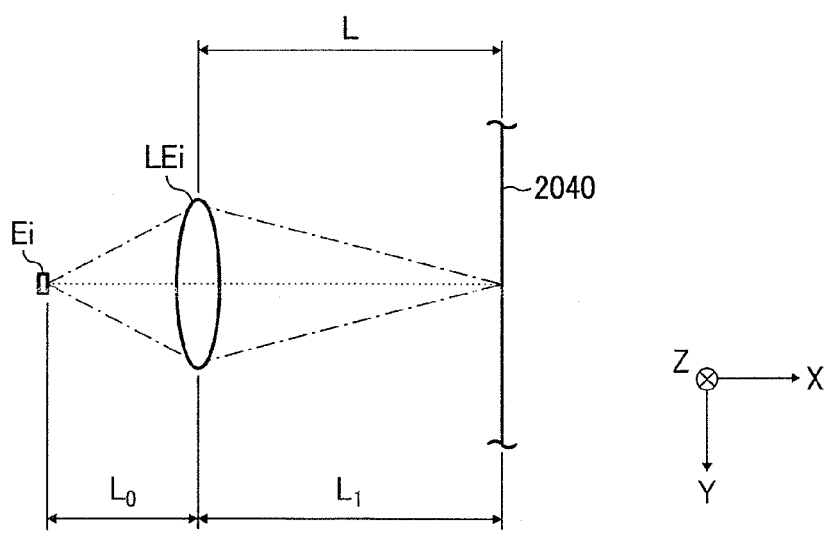
FIG. 21 is a first schematic diagram of a lighting collective lens.

When, as shown in FIG. 21 for example, the detection light is focused on the transfer belt 2040, the following equation (2) is satisfied:

$$B = mS \tag{2}$$

From both the above inequality (1) and the above equation (2), the relation between the lateral magnification m and the arrangement pitch P of the light-emitting elements is expressed as the following inequality (3):

$$mS \leq P \tag{3}$$

The above inequality (3) is then transformed to the following inequality (4):

$$m \leq P/S \tag{4}$$

As can be seen from this, to suppress a decrease in the accuracy of detection, it is necessary to set the lateral magnification m of the lighting collective lens LEi less than or equal to the arrangement pitch P of the light-emitting elements divided by the area S of the light-emitting surface of the light-emitting element.

If the focal distance of the lighting collective lens LEi is f, the distance between the light-emitting element Ei and the lighting collective lens LEi is $L_0$, and the distance between the lighting collective lens LEi and the focus position is $L_1$, then the relation among f, $L_0$, and $L_1$ satisfies the following equation (5). The letter L shown in FIG. 21 indicates the distance between the lighting collective lens LEi and the transfer belt 2040. In this example, $L = L_1$.

$$1/L_0 + 1/L_1 = 1/f \tag{5}$$

Moreover, at the lighting collective lens LEi, the relation among the lateral magnification m, the distance $L_0$, and the distance $L_1$ satisfies the following equation (6).

$$m = L_1/L_0 \tag{6}$$

The above equation (5) is transformed to the following equation (7) by using the relation of the above equation (6):

$$(1 + 1/m)/L_0 = 1/f \tag{7}$$

Therefore, the lighting collective lens LEi with the focal distance f and a lateral magnification m that satisfies the above inequality (4) is arranged so that the distance $L_0$ from the light-emitting element Ei satisfies the above equation (7).

When checking an enlarged view of the toner pattern, it is found that the toner density varies within even one pattern. Therefore, if the spot size B of the detection light on the transfer belt 2040 is too small, an accurate detection may not be conducted.

Moreover, as the light-emitting element, a light-emitting element that receives a high density current and has a high luminous efficiency is preferably used. More particularly, an LED array that includes small light-emitting elements from several tens micrometers to one hundred micrometers is preferable. In the present embodiment, an LED array is used that includes 40-micrometer squared light-emitting elements arranged at the arrangement pitch of 400 μm. In this case, P/S=10.

The lighting collective lens LEi is preferably a magnifier. Usage of a magnifier as the lighting collective lens LEi is effective to reduce the size of the reflective optical sensor.

Even when the lateral magnification m satisfies the above inequality (4), as the distance increases between the reflective optical sensor and the transfer belt 2040, it is necessary to attach the reflective optical sensor and the optical elements of the reflective optical sensor at more accurate positions. Moreover, a long distance between the reflective optical sensor and the transfer belt 2040 makes it difficult to maintain the intensity of light received at the light-receiving elements at a sufficient level. These, eventually, may prevent size reduction of the reflective optical sensor. Therefore, with various conditions taken into consideration such as manufacturing costs and the state of the area where the reflective optical sensors are arranged in the image forming apparatus, the lateral magnification m is, more preferably, less than 10.

In the present embodiment, the lighting collective lens has the lateral magnification m of 8. That is, the above relation expressed by Inequality (4) is satisfied.

As long as the above relation expressed by Inequality (1) is satisfied, it is unnecessary to focus the detection light on the transfer belt 2040.

Figure 22:
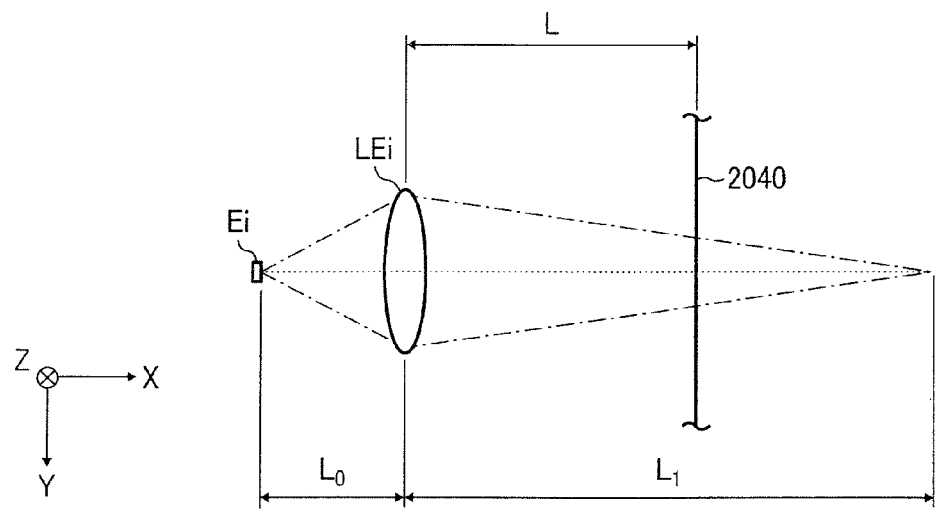
FIG. 22 is a second schematic diagram of the lighting collective lens.

For example, as shown in FIG. 22, the distance $L_1$ can be longer than the distance L. In this case, the spot size B on the transfer belt 2040 is larger than mS (B>mS). Satisfaction of B≤P leads to mS<B≤P, which further leads to m<P/S.

Figure 23:
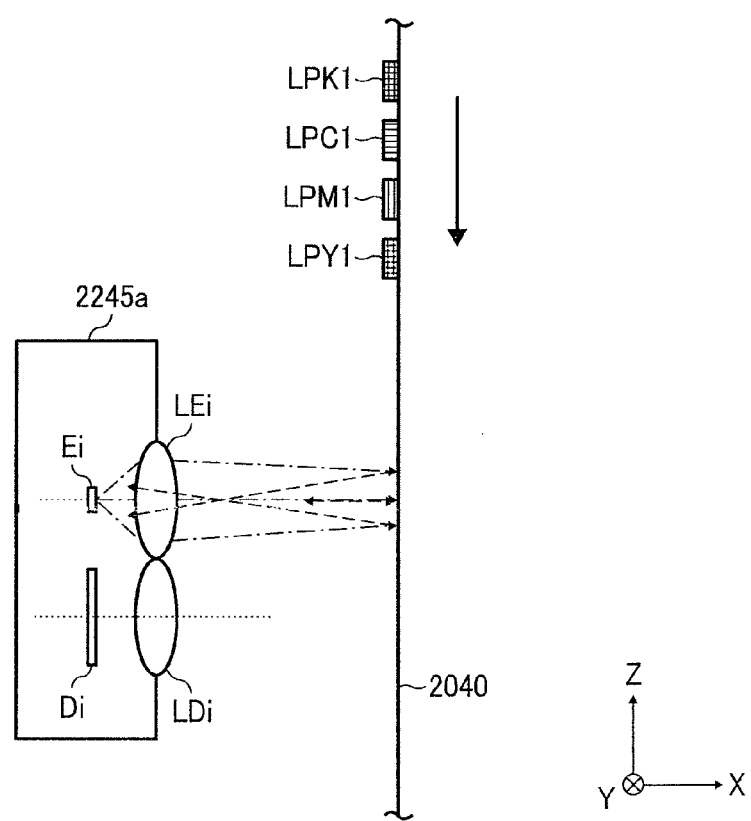
FIG. 23 is a schematic diagram that explains a situation where an axis that passes through the center of the light-emitting surface of a light-emitting element and is perpendicular to the light-emitting surface is aligned with the optical axis of the lighting collective lens.

If the optical axis of the lighting collective lens LEi is aligned with the axis that passes through the center of the light-emitting surface and is perpendicular to the light-emitting surface of the light-emitting element Ei, most of the beam of light reflected from the transfer belt 2040 may not strike the light-receiving element Di (see FIG. 23). If so, the difference caused by the reflection characteristics of the transfer belt 2040 and the reflection characteristics of the toner pattern decreases, which decreases both the accuracy of pattern-position detection and the accuracy of toner-density detection.

Figure 24:
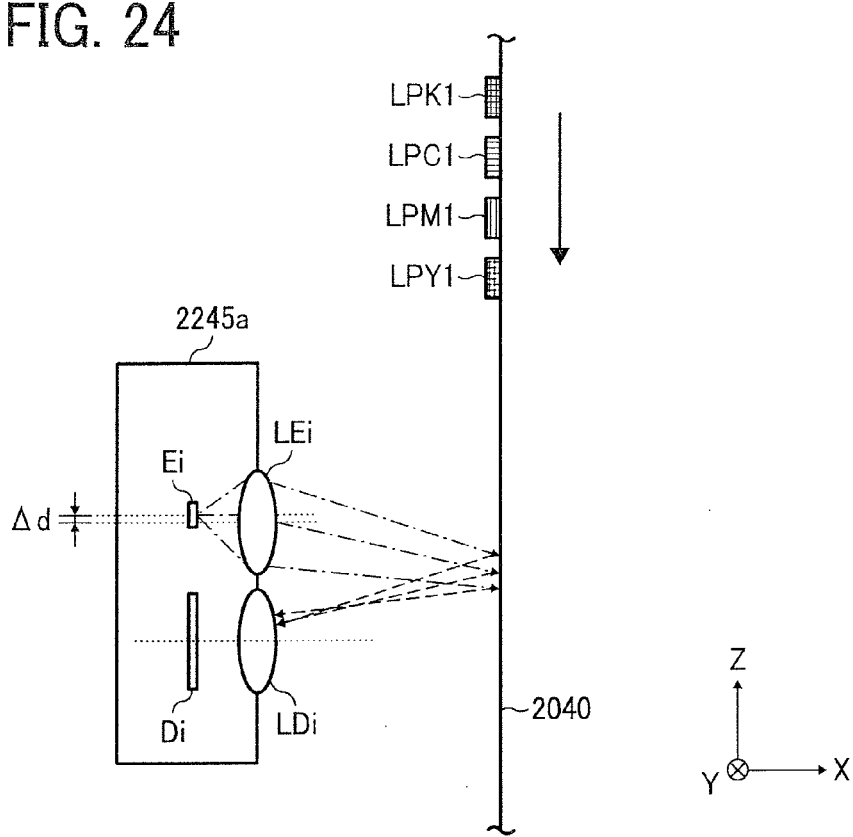
FIG. 24 is a schematic diagram that explains a shift of the lighting collective lens.

Therefore, as shown in FIG. 24 for example, the optical axis of the lighting collective lens LEi is shifted by Δd in the −Z direction so as to increase the beam of light received at the light-receiving element. In this example, Δd is 0.04 mm that corresponds to about 10% of the diameter of the lighting collective lens LEi.

Figure 25:
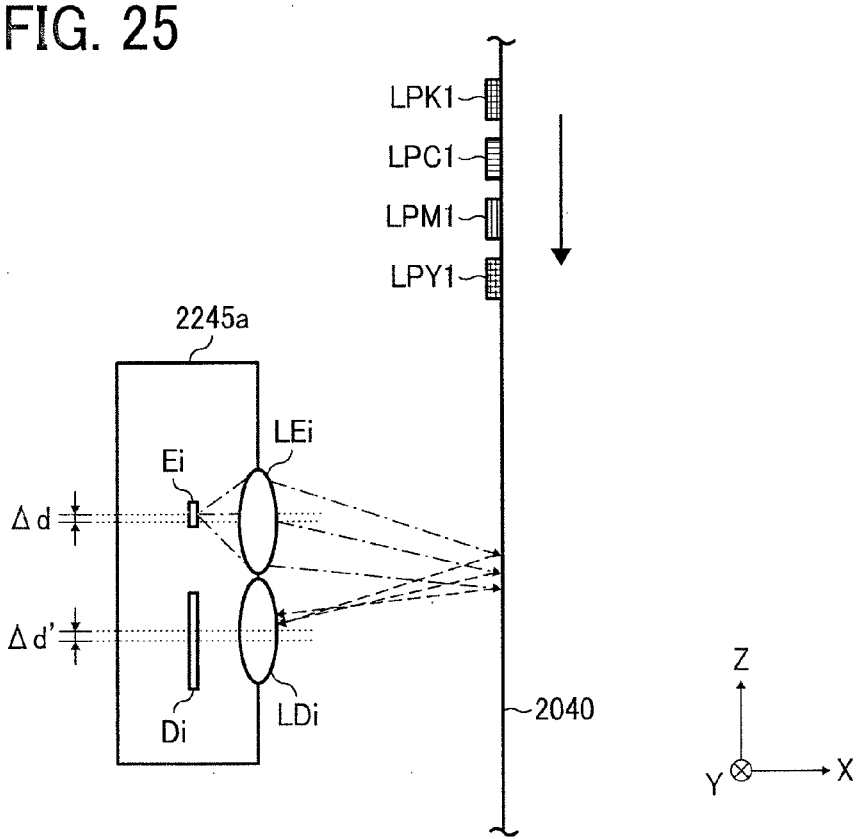
FIG. 25 is a schematic diagram that explains a shift of the light receiving collective lens.

Moreover, as shown in FIG. 25 for example, if the light receiving collective lens LDi is shifted by Δd' in the +Z direction, the light receiving collective lens LDi can collect a higher intensity of light beam and guides the light beam to the light-receiving element Di.

At least one of the lighting collective lens LEi and the light receiving collective lens LDi can be any of a spherical lens that has powers in both the Y-axis direction and the Z-axis direction, a cylindrical lens that has a positive power only in the Z-axis direction, and an anamorphic lens that has a first power in the Y-axis direction and a second power in the Z-axis direction in which the first power is different from the second power.

Figure 26:
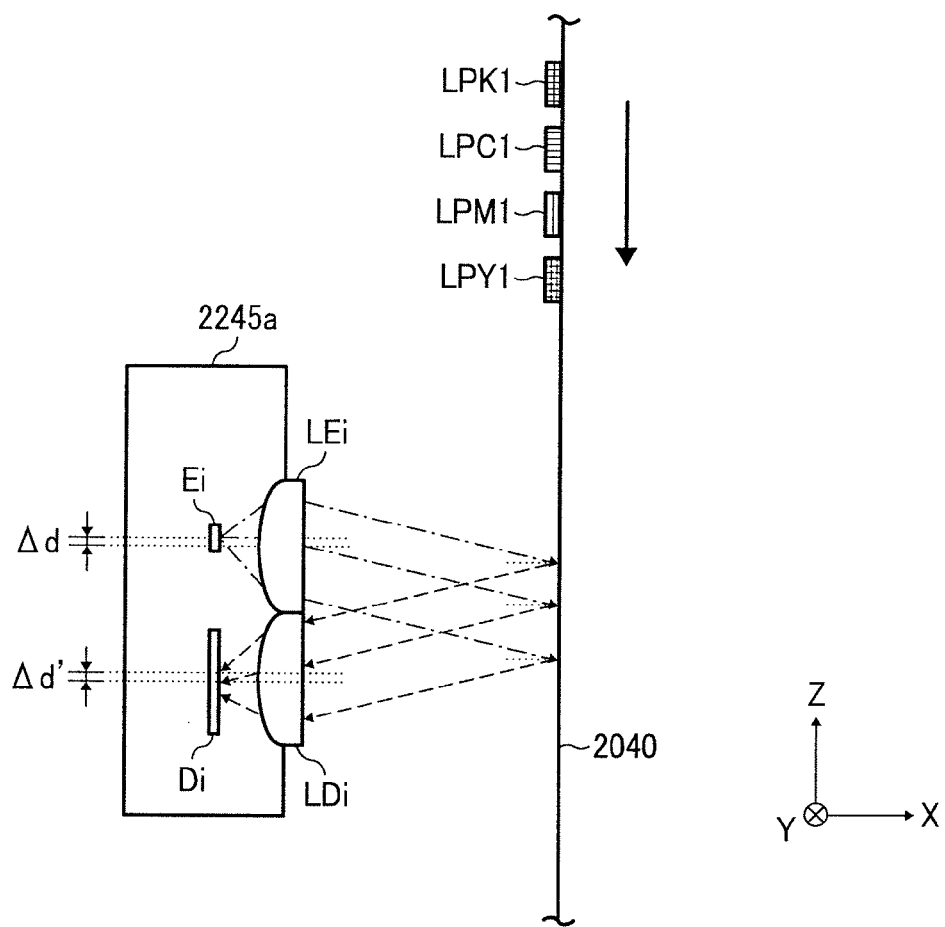
FIG. 26 is a schematic diagram of a modification of the collective lens.
Figure 27:
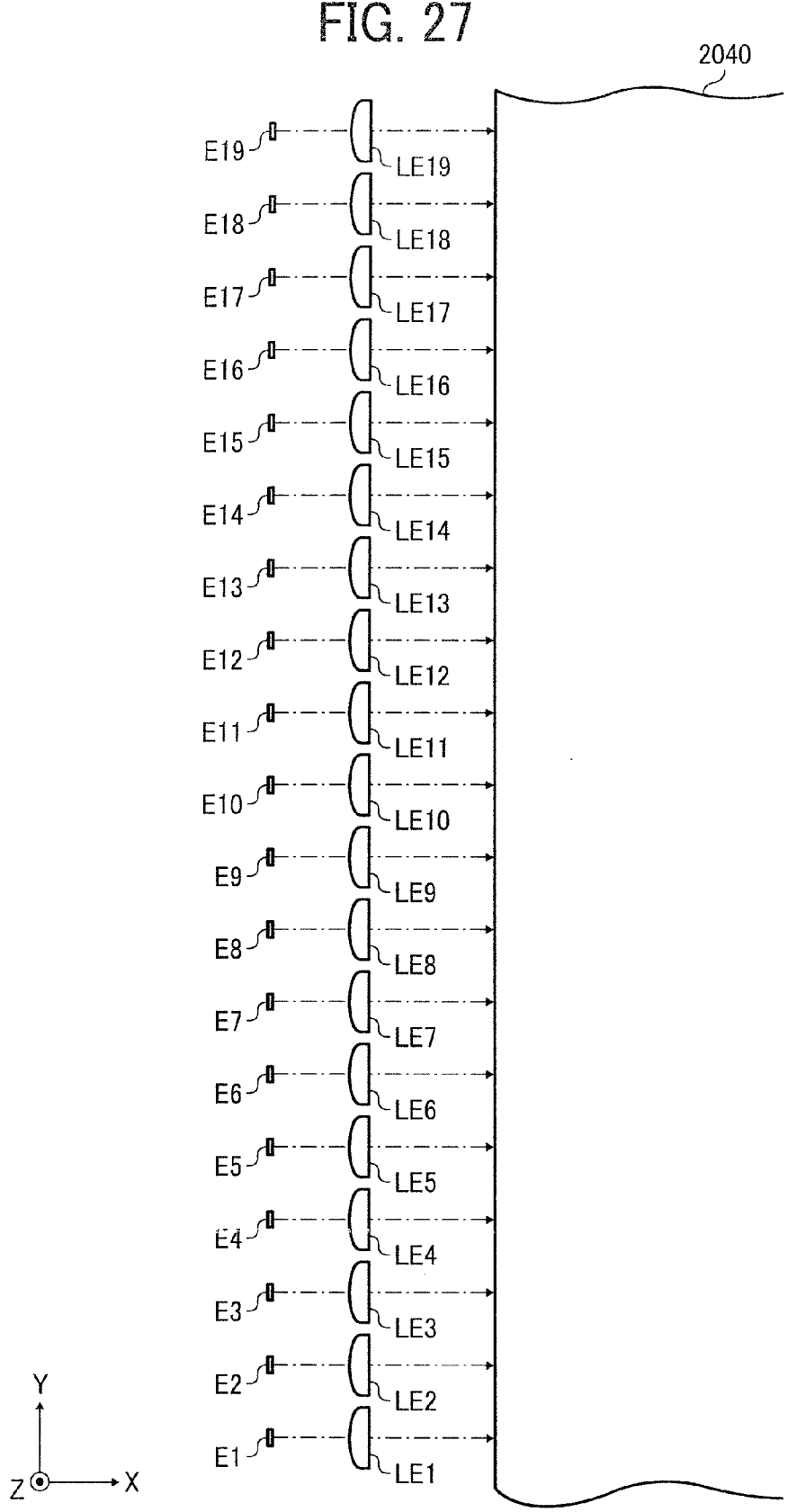
FIG. 27 is a schematic diagram of a modification of the lighting collective lens.
Figure 28:
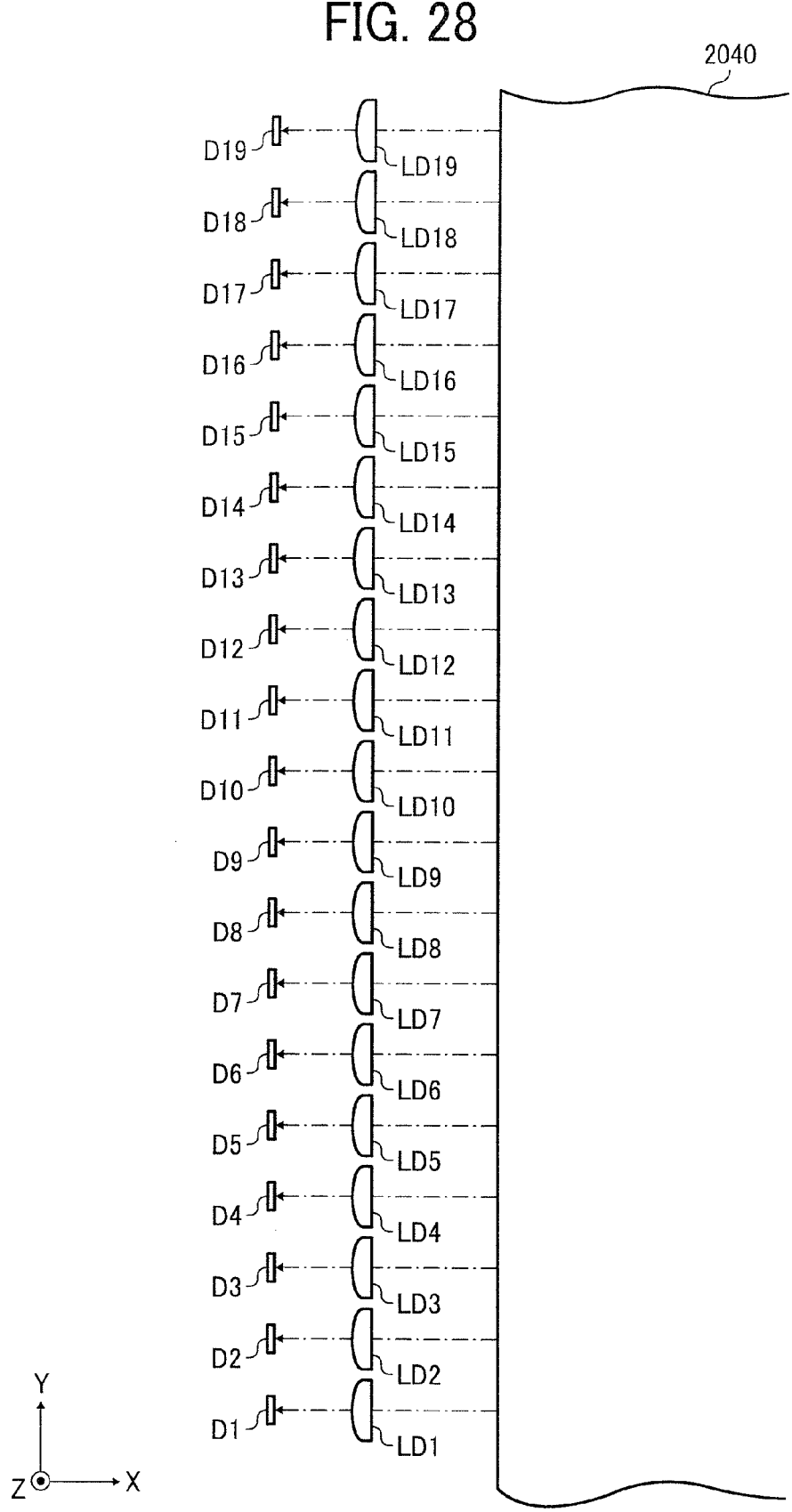
FIG. 28 is a schematic diagram of a modification of the light receiving collective lens.

Moreover, as shown in FIGS. 26 to 28 for example, the above spherical lens can be a lens that has a light-receiving surface with a light collecting power and a light-existing surface with no light collecting power.

Figure 29:
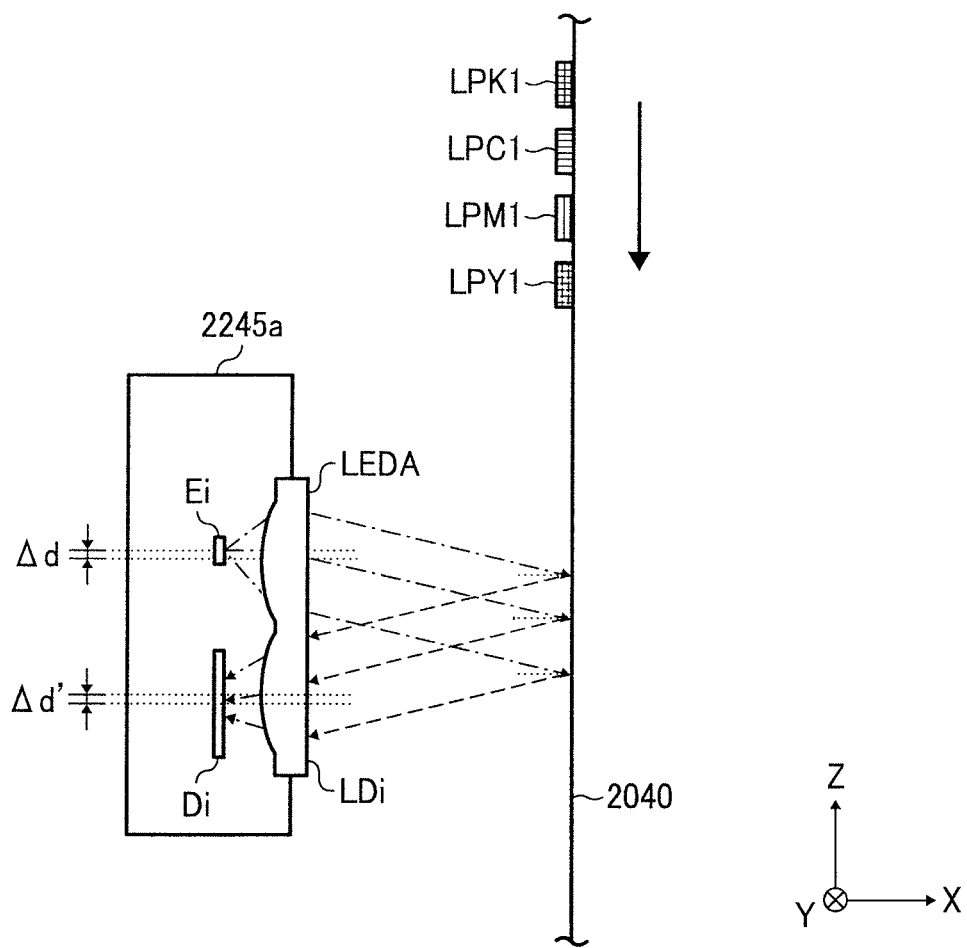
FIG. 29 is a first schematic diagram of the lighting collective lens and the light receiving collective lens that are formed as one unit.
Figure 30:
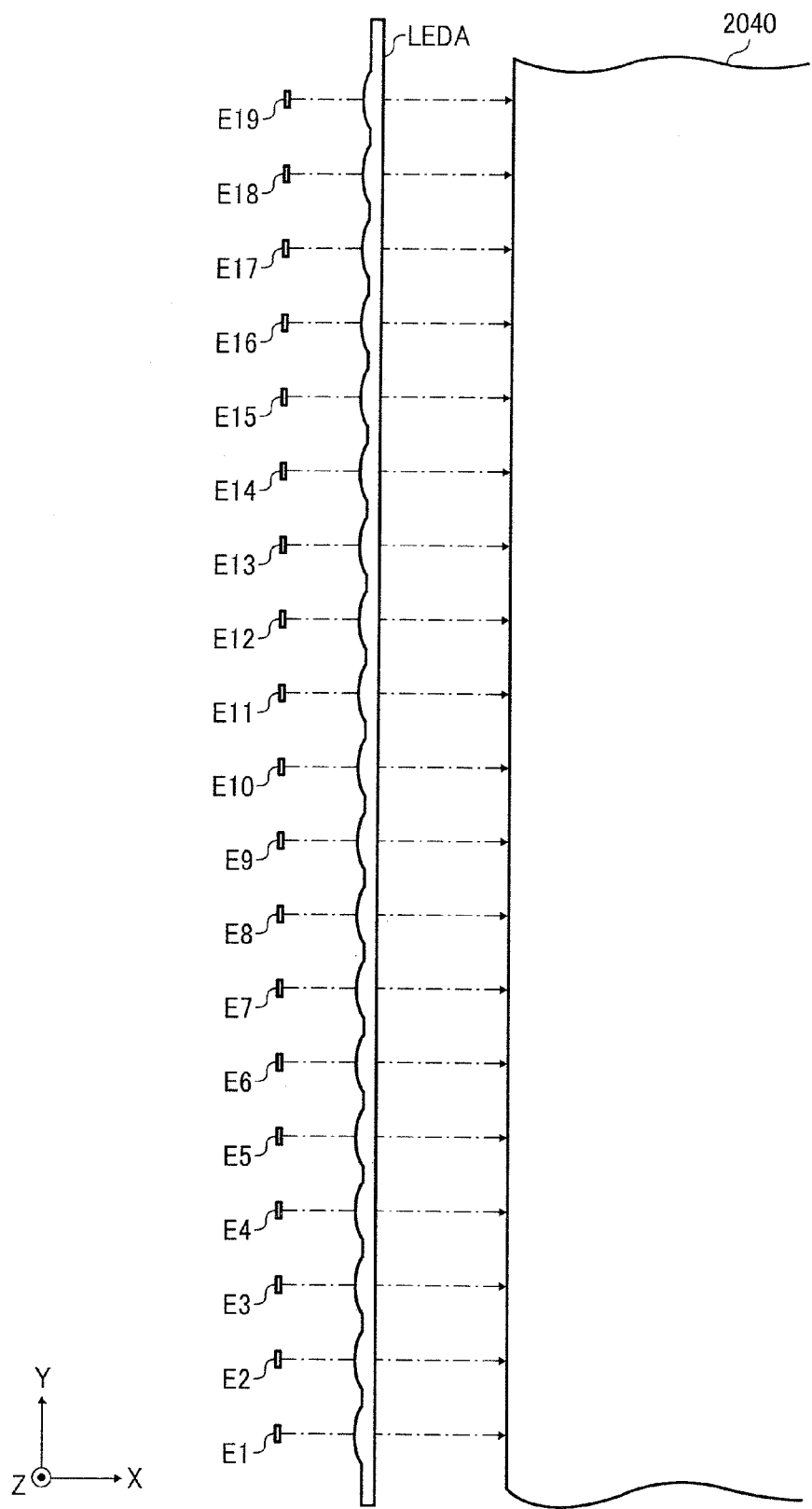
FIG. 30 is a second schematic diagram of the lighting collective lens and the light receiving collective lens that are formed as one unit.
Figure 31:
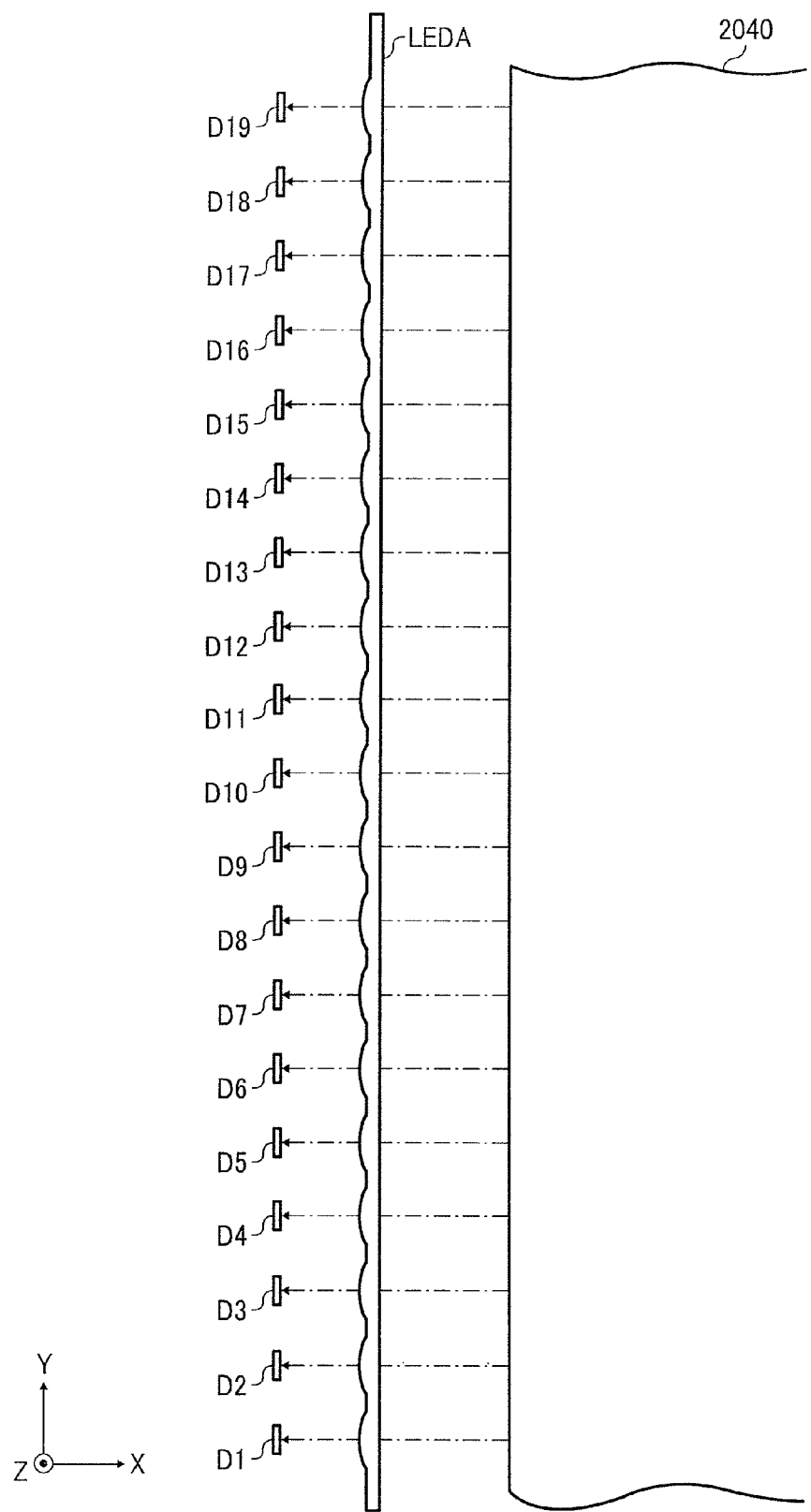
FIG. 31 is a third schematic diagram of the lighting collective lens and the light receiving collective lens that are formed as one unit.
Figure 32A:
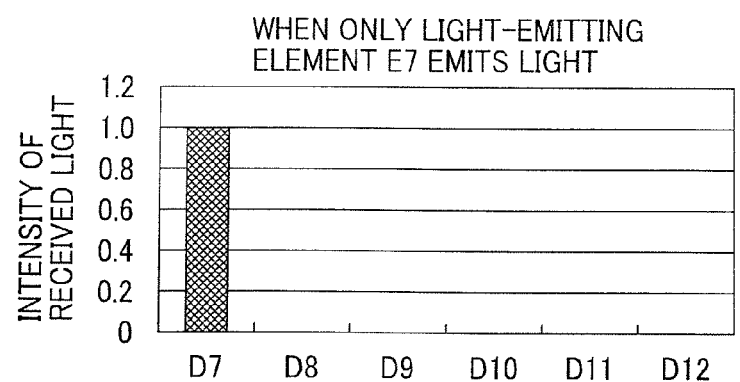
FIGS. 32A to 32F are graphs of the intensities of light received at the light-receiving elements (D7 to D12) when different beams of detection light (S7 to S12) are reflected from the surface of the transfer belt.
Figure 32B:
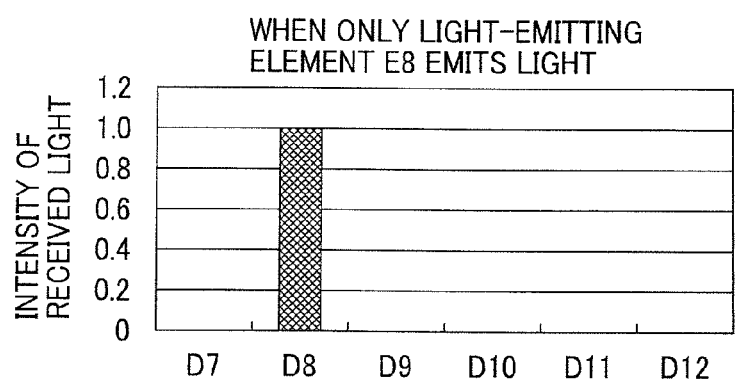
Figure 32C:
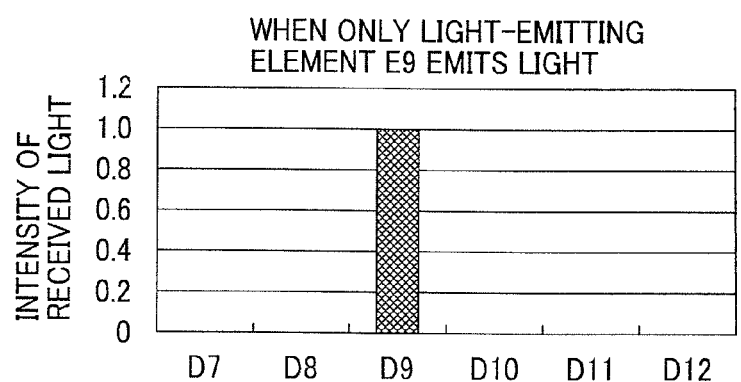
Figure 32D:
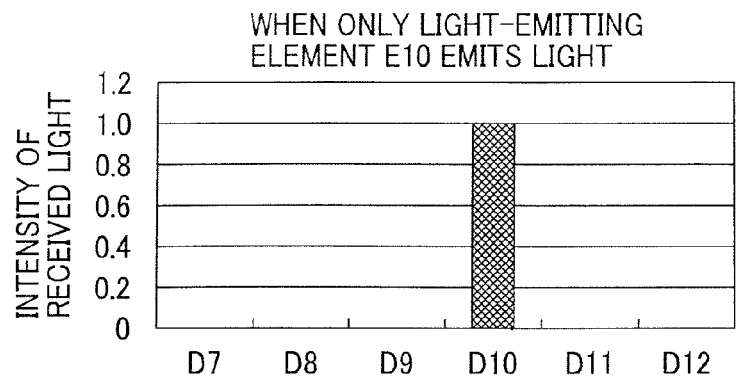
Figure 32E:
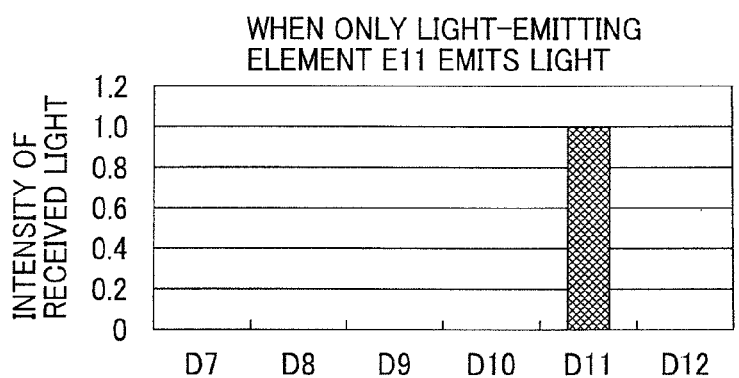
Figure 32F:
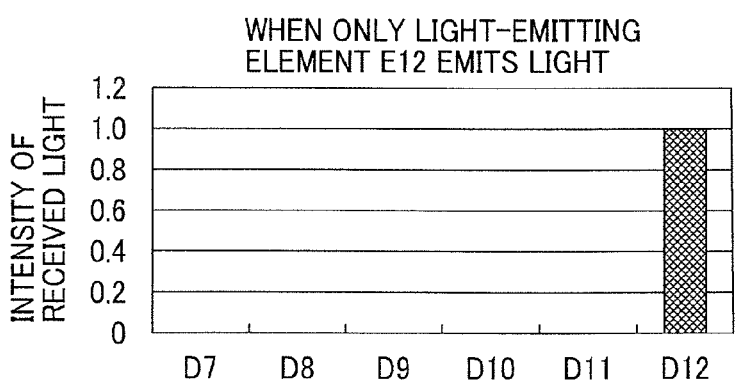
Figure 33:
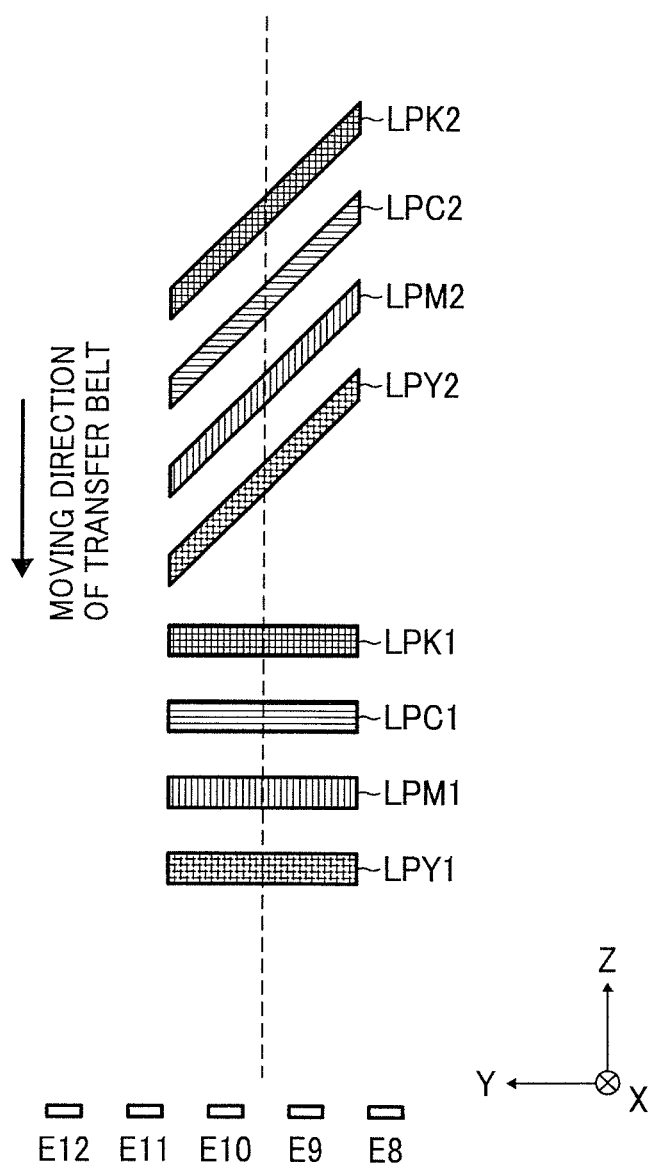
FIG. 33 is a first schematic diagram that explains a position detecting process.

Moreover, as shown in FIGS. 29 to 31 for example, the lighting optical system and the light receiving optical system can be formed as one unit called "lighting/light receiving optical system LEDA". This will improve the production efficiency of the reflective optical sensor. This will also increase the accuracy of arrangement between the lens surfaces. Each lens surface can be formed on a glass substrate or a resin substrate using a technique such as photolithography or nanoinprint.

The position detecting process and the density detecting process using the toner detector 2245 are described below. The reflective optical sensor shown in FIGS. 29 to 31 is used in these processes. It is assumed that when the light-emitting element Ei emits the detection light Si and the detection light Si is specularly reflected from the transfer belt 2040, the intensity of light received at the light-receiving element Di is 1 (see FIGS. 32A to 32F).

Moreover, as the position detection pattern reaches the position irradiated by the detection light coming from the reflective optical sensor earlier than the density detection pattern (see FIG. 7), the position detecting process is performed prior to the density detecting process. From the designing perspective, the toner pattern is formed in such a manner that the center position between the light-emitting elements E9 and E10 is aligned with the center position of the toner pattern in the main direction and the formed toner pattern is transferred onto the transfer belt 2040 (see FIG. 33).

<<Position Detecting Process>>

The printer control device 2090 causes the light-emitting element E10 to emit light continuously in accordance with the time when the position detection pattern PP comes close to the reflective optical sensor. The detection light emitted from the light-emitting element El0 irradiates the line patterns LPY1 to LPK2 sequentially by rotation of the transfer belt 2040 (see FIG. 34A).

Figure 34A:
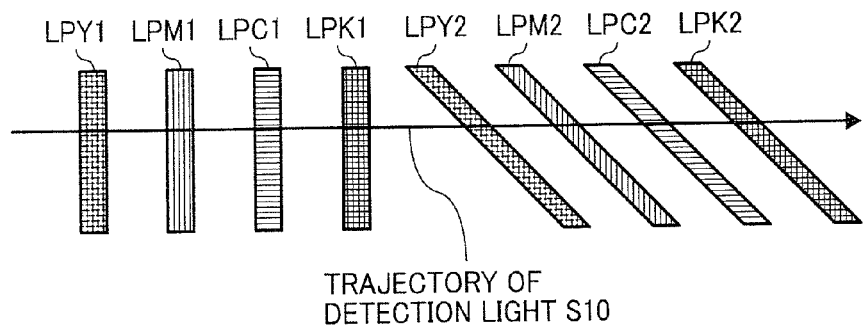
FIGS. 34A and 34B are second schematic diagrams that explain the position detecting process.
Figure 34B:
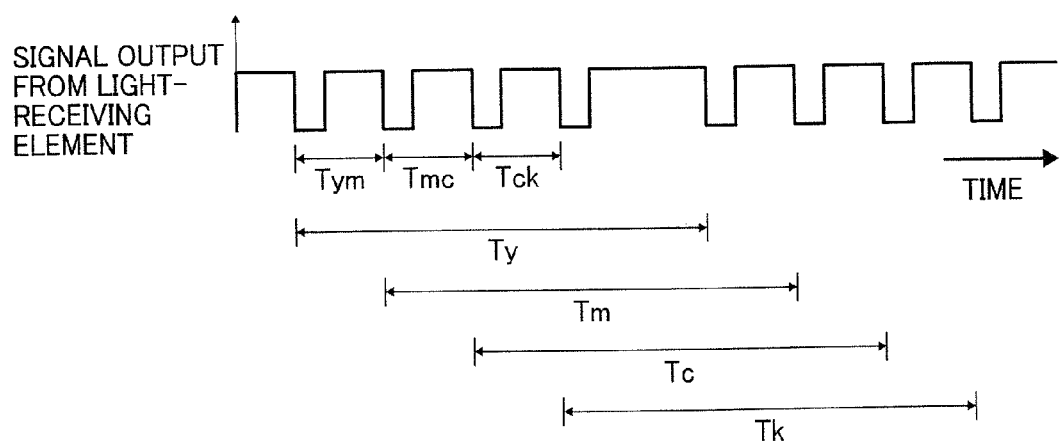
Figure 35A:
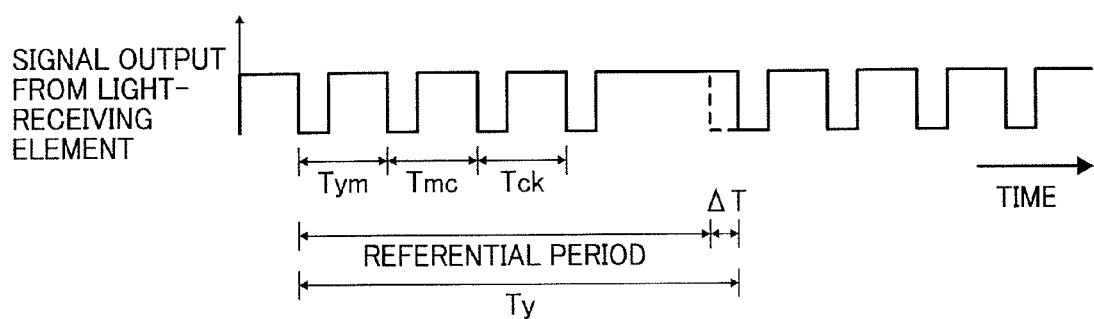
FIGS. 35A and 35B are third schematic diagrams that explain the position detecting process.
Figure 35B:
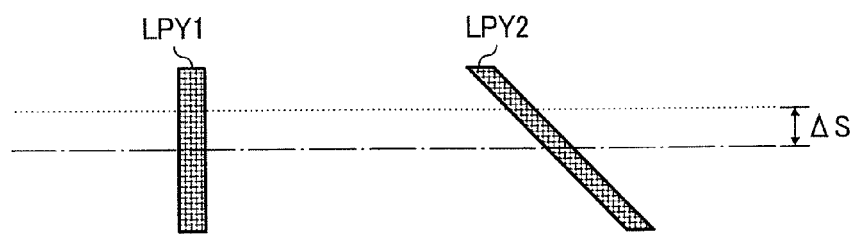

The printer control device 2090 traces the signal output from each light-receiving element in chronological order and calculates periods Tym, Tmc, and Tck, where the period Tym is the period between when the detection light irradiates the line pattern LPY1 and when it irradiates the line pattern LPM1, the period Tmc is the period between when the detection light irradiates the line pattern LPM1 and when it irradiates the line pattern LPC1, and the period Tck is the period between when the detection light irradiates the line pattern LPC1 and when it irradiates the line pattern LPK1 (see FIG. 34B).

If the periods Tym, Tmc, and Tck are substantially equal, the printer control device 2090 determines that the positional relation between the toner images in the sub direction is correct. If the periods Tym, Tmc, and Tck are not substantially equal, the printer control device 2090 determines that the positional relation between the toner images in the sub direction is incorrect. If the positional relation is incorrect, the printer control device 2090 calculates an amount of misalignment in the above positional relation using the differences among the periods Tym, Tmc, and Tck, and informs the amount of misalignment to the scanning control device. The scanning control device adjusts the point of time when each station starts scanning so that the amount of misalignment is set to zero.

The printer control device 2090 also calculates periods Ty, Tm, Tc, and Tk, where the period Ty is the period between when the detection light irradiates the line pattern LPY1 and when it irradiates the line pattern LPY2, the period Tm is the period between when the detection light irradiates the line pattern LPM1 and when it irradiates the line pattern LPM2, the period Tc is the period between when the detection light irradiates the line pattern LPC1 and when it irradiates the line pattern LPC2, and the period Tk is the period between when the detection light irradiates the line pattern LPK1 and when it irradiates the line pattern LPK2 (see FIG. 34B).

The printer control device 2090 compares the periods Ty, Tm, Tc, and Tk with predetermined referential periods. If the periods Ty, Tm, Tc, and Tk are equal to the referential periods, the printer control device 2090 determines that the positional relation between the toner images in the main direction is correct.

If, for example, the period Ty is different from its referential period, the printer control device 2090 calculates the amount of misalignment of the yellow toner image in the main direction using the following equation (8) as an amount of misalignment $\Delta S$ (see FIGS. 35A and 35B), where V is the velocity of the transfer belt 2040 in the sub direction, $\Delta T$ is the difference between the period Ty and the referential period, and $\theta$ is the angle formed between the line pattern LPY2 and the main direction. The amount of misalignment $\Delta S$ is informed to the scanning control.

$$\Delta S = V \cdot \Delta T \cdot \cot \theta \qquad (8)$$

The scanning control device then adjusts the Y station so that the amount of misalignment $\Delta S$ is set to zero.

The printer control device 2090 calculates, using the amount of misalignment $\Delta S$, the center position of the toner pattern in the main direction.

It is allowable to cause two or more light-emitting elements to emit light one after another at a high speed. Suppose the case, for example, the three light-emitting elements (E9, E10, and E11) emit light one after another in the order of E9, E10, E11, E9, E10 . . . In this case, the printer control device 2090 calculates an average of the signal output from each light-receiving element when the light-emitting elements E9 emits light, the signal output from each light-receiving element when the light-emitting element El0 emits light, and the signal output from each light-receiving element when the light-emitting elements E11 emits light and then calculates the amount of misalignment using the average of the output signals. This configuration will improve the accuracy of detection.

<<Density Detecting Process>>

For example, during the above position detecting process, it is determined that the center position of the toner pattern in the main direction is between the light-emitting elements E9 and E10.

Figure 36:
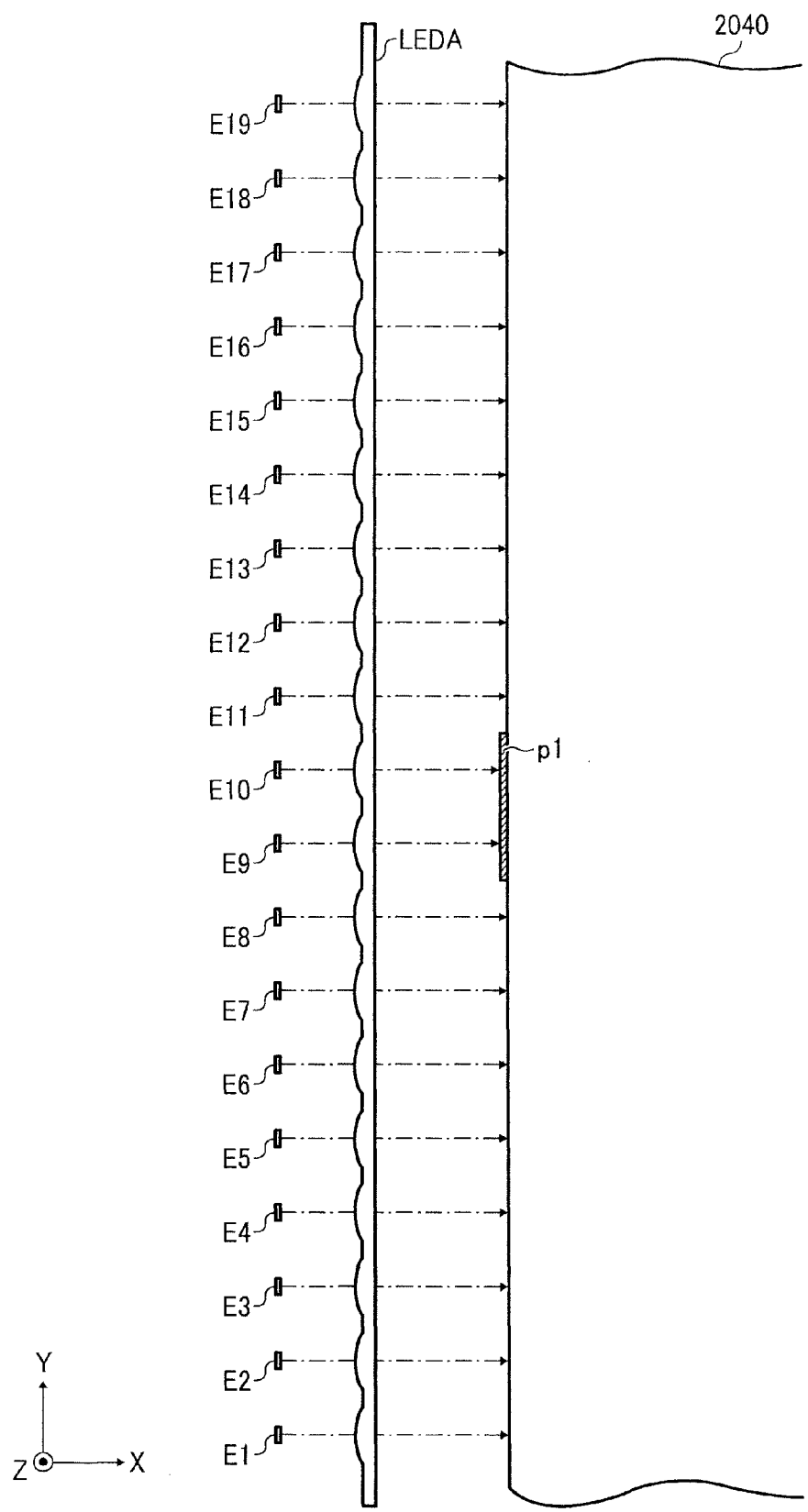
FIG. 36 is a first schematic diagram that explains a density detecting process.

As shown in FIG. 36 for example, when the rectangular pattern comes in front of the reflective optical sensor, the printer control device 2090 causes the light-emitting elements E9 and E10 to emit light in a sequential and repeated manner.

Figure 37:
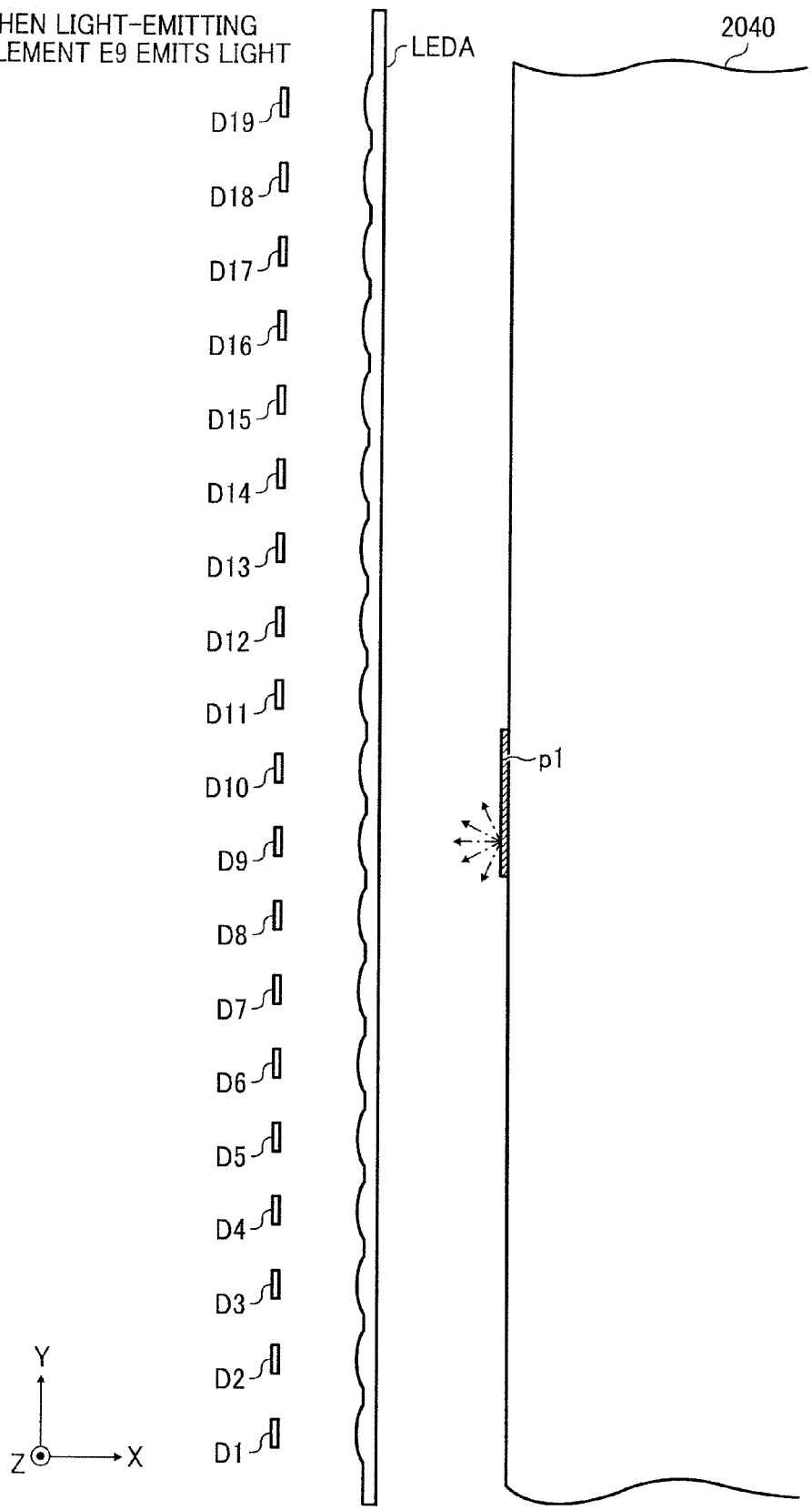
FIG. 37 is a second schematic diagram that explains the density detecting process.
Figure 38:
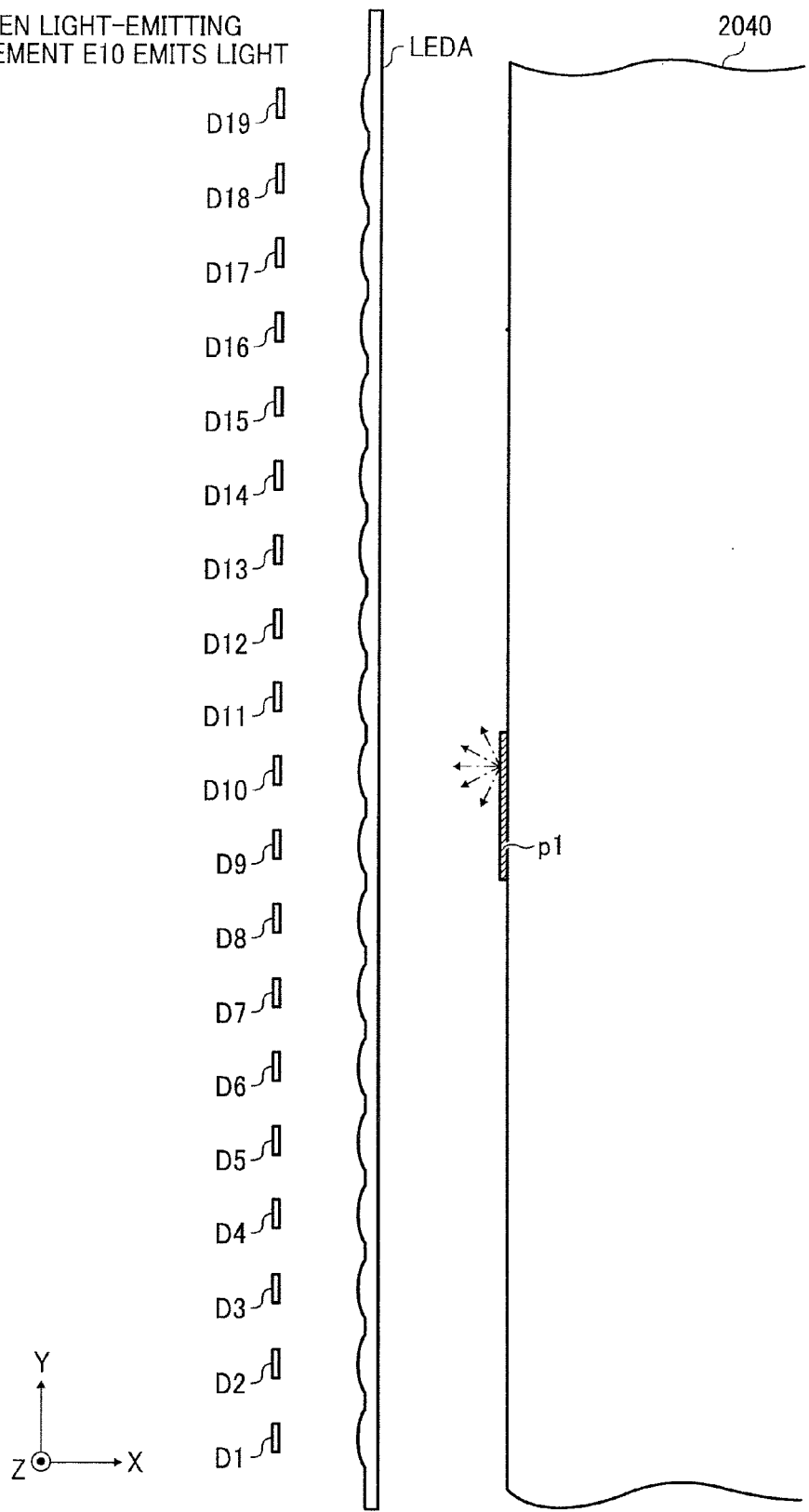
FIG. 38 is a third schematic diagram that explains the density detecting process.

As shown in FIGS. 37 and 38 for example, each of the beams of detection light S9 and S10 is reflected both specularly and diffusely from the surface of the rectangular pattern. Herein, light, which is specularly reflected, is called "specularly reflected light" and light, which is diffusely reflected, is called "diffusely reflected light".

Figure 39A:
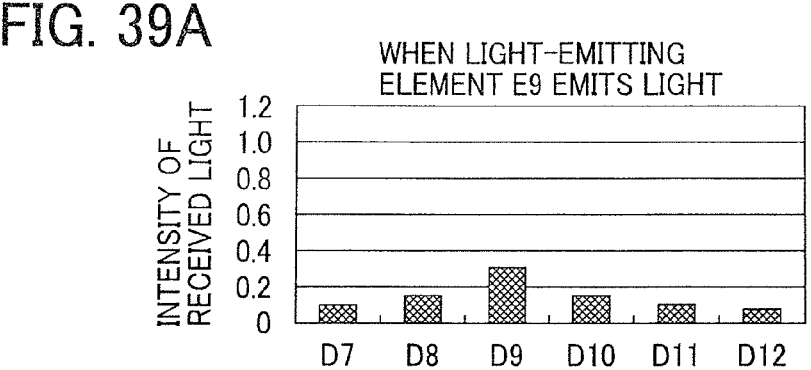
FIG. 39A is a graph of the intensities of light received at the light-receiving elements (D7 to D12) when the beam of detection light S9 is reflected from the density detection pattern during the density detecting process.

The processing device of each reflective optical sensor calculates, in accordance with the signal output from the corresponding light-receiving element when the detection light S9 irradiates the rectangular pattern, the intensity of light received at the corresponding light-receiving element and stores the calculated intensity in a memory (not shown) as the detected intensity of received light. Further, The processing device of each reflective optical sensor calculates, in accordance with the signal output from the corresponding light-receiving element when the detection light S10 irradiates the rectangular pattern, the intensity of light received at the corresponding light-receiving element and stores the calculated intensity in a memory (not shown) as the detected intensity of received light FIG. 39A is a graph of the intensity of light received at each light-receiving element when the detection light S9 irradiates the rectangular pattern. As compared with the situation where the detection light S9 irradiates the transfer belt 2040, light specularly reflected and received at the light-receiving element D9 decreases, while light diffusely reflected is received at the light-receiving elements other than the light-receiving element D9.

Figure 39B:
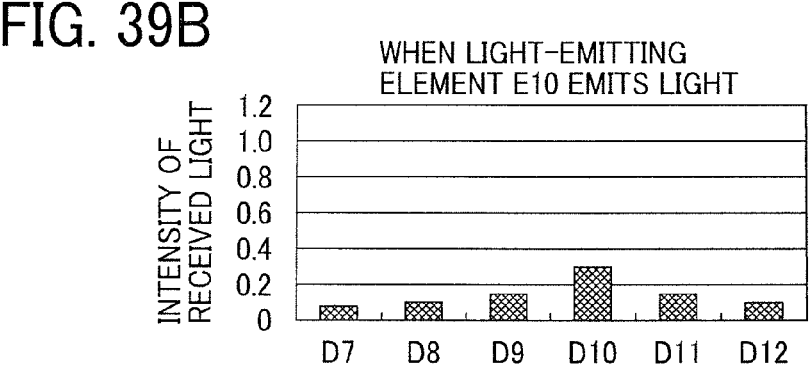
FIG. 39B is a graph of the intensities of light received at the light-receiving elements (D7 to D12) when the beam of detection light S10 is reflected from the density detection pattern during the density detecting process.

FIG. 39B is a graph of the intensity of light received at each light-receiving element when the detection light S10 irradiates the rectangular pattern. In this situation, as compared with the situation where the detection light S10 irradiates the transfer belt 2040, light specularly reflected and received at the light-receiving element D10 decreases, while light diffusely reflected is received at the light-receiving elements other than the light-receiving element D10.

In general, light specularly reflected from a rectangular pattern decreases in proportion to the increase of the toner density of the rectangular pattern, while light diffusely reflected from a rectangular pattern increases in proportion to the increase of the toner density of the rectangular pattern.

Figure 40A:
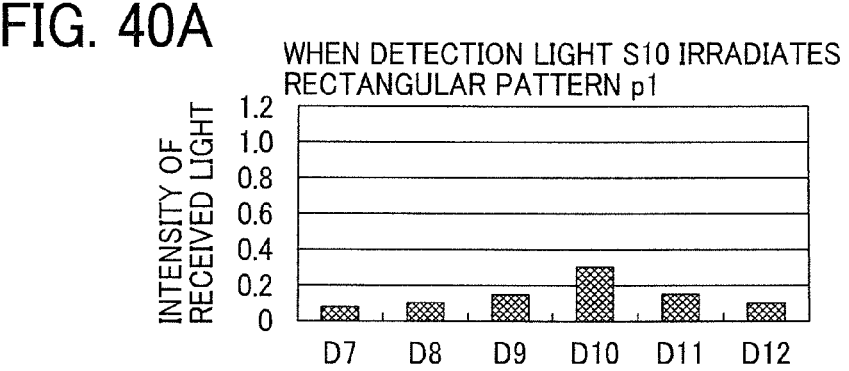
FIGS. 40A to 40E are graphs of the intensities of light received at the light-receiving elements (D7 to D12) when the beam of detection light S10 is reflected from different rectangular patterns.
Figure 40B:
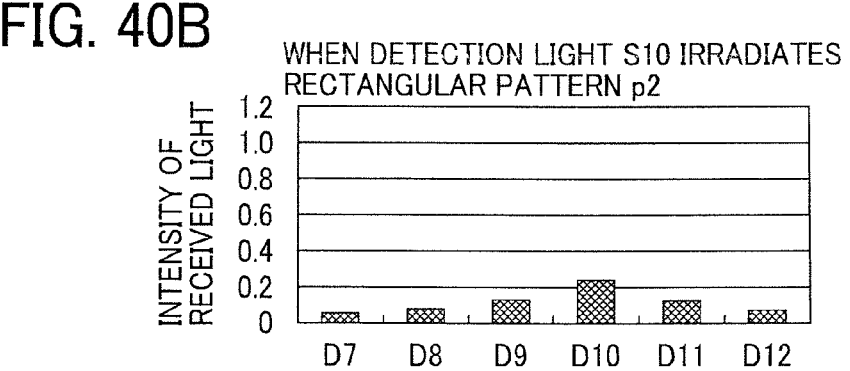
Figure 40C:
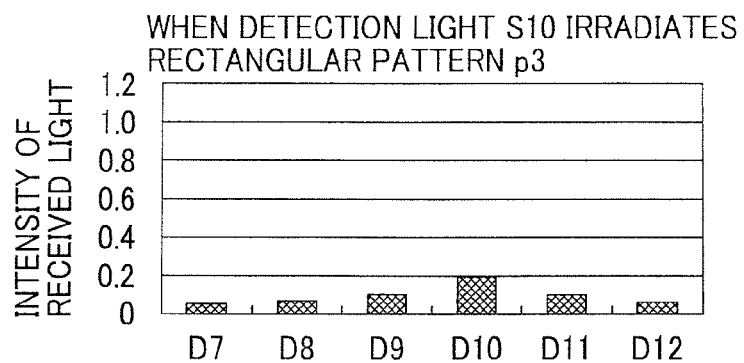
Figure 40D:
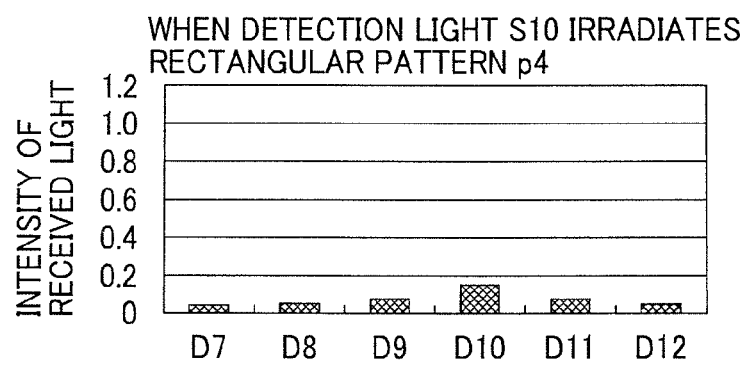
Figure 40E:
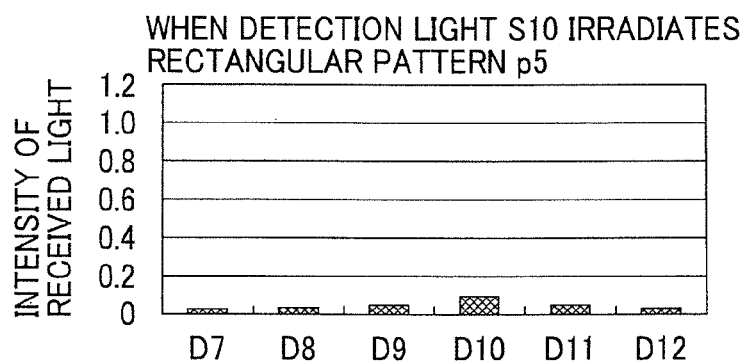

FIG. 40A is an example of a graph of the intensities of light received at the light-receiving elements D7 to D12 when the detection light S10 irradiates the rectangular pattern p1. FIG. 40B is an example of a graph of the intensities of light received at the light-receiving elements D7 to D12 when the detection light S10 irradiates the rectangular pattern p2. FIG. 40C is an example of a graph of the intensities of light received at the light-receiving elements D7 to D12 when the detection light S10 irradiates the rectangular pattern p3. FIG. 40D is an example of a graph of the intensities of light received at the light-receiving elements D7 to D12 when the detection light S10 irradiates the rectangular pattern p4. FIG. 40E is an example of a graph of the intensities of light received at the light-receiving elements D7 to D12 when the detection light S10 irradiates the rectangular pattern p5. It is clear from the graphs that, as the toner density increases, the intensity of light received at each light-receiving element decreases.

The printer control device 2090 determines, based on the intensity of detected light that is informed from the processing device of the reflective optical sensor 2245a, whether the yellow toner density is appropriate; determines, based on the intensity of detected light that is informed from the processing device of the reflective optical sensor 2245b, whether the magenta toner density is appropriate; determines, based on the intensity of detected light that is informed from the processing device of the reflective optical sensor 2245c, whether the cyan toner density is appropriate; and determines, based on the intensity of detected light that is informed from the processing device of the reflective optical sensor 2245d, whether the black toner density is appropriate. If the toner density is not appropriate, the printer control device 2090 adjusts the developing system of the corresponding station so that the toner density is adjusted to an appropriate value.

As described above, the color printer 2000 according to the present embodiment includes the four photosensitive elements (2030a, 2030b, 2030c, and 2030d); the optical scanning device that scans the photosensitive elements (2030a, 2030b, 2030c, and 2030d) in the main-scanning direction with the beams of light modulated in accordance with the image data and forms a latent image on the surface of each photosensitive element; the four developing rollers (2033a, 2033b, 2033c, and 2033d) each being used to attach toner to the latent image, thereby forming a toner image; the transfer roller 2042 that transfers the toner images to the transfer belt 2040; the toner detector 2245 that detects the position of the toner pattern formed on the transfer belt 2040 in both the main direction and the sub direction and the toner density of the toner pattern; the printer control device 2090 that totally controls the color printer 2000; etc.

The toner detector 2245 includes the four reflective optical sensors (2245a, 2245b, 2245c, and 2245d).

Each reflective optical sensor includes the 19 light-emitting elements (E1 to E19) that are arranged in a row along the Y-axis direction and emit the beams of light toward the transfer belt 2040; the 19 lighting collective lenses (LE1 to LE19) that guide the beam of light emitted from the corresponding light-emitting element to the surface of the transfer belt 2040; the 19 light receiving collective lenses (LD1 to LD19) that collect the beam of light reflected from the transfer belt 2040 or the toner pattern and guide the beam of light to the corresponding light-receiving element; the 19 light-receiving elements (D1 to D19) that receive the beam of light reflected from the transfer belt 2040 or the toner pattern; and the processing device.

Each collective lens has the lateral magnification m that satisfies m≤P/S, where S is the size of the light-emitting element and P is the arrangement pitch of the light-emitting elements. This enables, even if the toner pattern is smaller than the conventional toner pattern, size reduction of the reflective optical sensor, while maintaining the intensity of light sufficient for the detection. Therefore, even if the toner pattern is small, an accurate position and an accurate toner density of the toner pattern can be detected.

The printer control device 2090 determines, based on the signals output from the light-receiving elements when the position detection pattern is irradiated by the detection light, whether the positional relation is appropriate in the sub direction and whether the positional relation is appropriate in the main direction, between the toner images. If the positional relation is not appropriate, the printer control device 2090 causes the scanning control device to adjust the positional relation.

The printer control device 2090 also determines, based on the signal output from each light-receiving element when the density detection pattern is irradiated by the detection light, whether the toner density is appropriate. If the toner density is not appropriate, the printer control device 2090 adjusts the developing system of the corresponding station so that the toner density becomes appropriate.

With this configuration, the color printer 2000 can maintain the high image quality without reducing the performance.

Moreover, because the reflective optical sensor according to the present embodiment is smaller than the conventional reflective optical sensor, a smaller printer can be produced as the color printer 2000.

Moreover, in the present embodiment, the size (area) of the toner pattern can be less than or equal to hundredth part of the size (area) of the conventional toner pattern; therefore, the amount of the non-contributing toner decreases remarkably. Thereby, time for replacement of the toner cartridge is extended.

In the above embodiment, the printer control device 2090 can be configured to calculate the center position of the density detection pattern in the main direction using the density detection pattern. This manner is described below briefly.

(1) When the position detecting process is completed, the printer control device 2090 causes the light-emitting elements E1 to E19 of each reflective optical sensor to emit light sequentially.

(2) The printer control device 2090 calculates, using the signal output from the light-receiving element Di when the light-emitting element Ei emits light, the intensity of light received at the light-receiving element Di.

(3) The printer control device 2090 determines the light-receiving element(s) having the intensity of received light less than 1. In the above embodiment, when the light-emitting element E9 emits light, the light-receiving elements D9 and D10 have the intensities of received light less than 1.

(4) The printer control device 2090 compares the intensity of light received at the light-receiving element D9 with the intensity of light received at the light-receiving element D10. If the intensity of light received at the light-receiving element D9 when the light-emitting element E9 emits light is less than the intensity of light received at the light-receiving element D10 when the light-emitting element E10 emits light, the printer control device 2090 determines that the center of the rectangular pattern is "closer to the light-emitting element E9 than the light-emitting element E10" in the main direction.

This positional detection is inferior to the positional detection using the position detection pattern from the perspective of accuracy; however, the position of density detection pattern in the main direction is detected with an accuracy corresponding to "the arrangement pitch of the light-emitting elements"

Moreover, it is allowable, in the above embodiment, to add another preparatory detection pattern to the density detection pattern so as to detect the position of the density detection pattern before the density detection.

Furthermore, although, in the above embodiment, the reflective optical sensor detects both the position and the toner density of the toner pattern, the configuration is not limited thereto. The reflective optical sensor can be configured to detect either the position or the toner density of the toner pattern.

Figure 41:
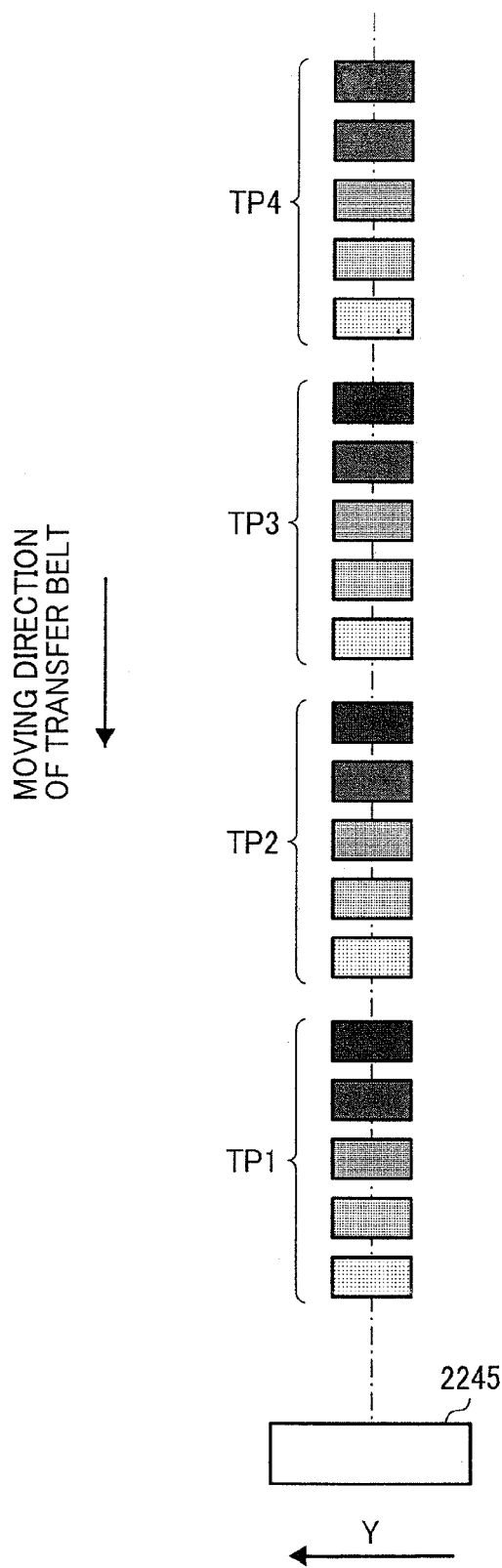
FIG. 41 is a schematic diagram of a modification of the toner pattern.

Moreover, in the above embodiment as shown in FIG. 41 for example, the toner patterns TP1 to TP4 can be arranged in a row along the moving direction of the transfer belt 2040. If only the toner-density detection is needed, one reflective optical sensor is enough for the toner detector 2245.

Furthermore, in the above embodiment, the printer control device 2090 can be configured to perform part or the entire of the process performed by the processing device of each reflective optical sensor.

Moreover, although in the above embodiment, the center position of the toner pattern is between the light-emitting elements E9 and E10 in the main direction, it is not limited thereto.

Furthermore, although in the above embodiment, each reflective optical sensor includes 19 light-emitting elements, the number of the light-emitting elements can be any value more than or equal to 3.

Moreover, although in the above embodiment, the 19 light-emitting elements (E1 to E19) are arranged in a row along the Y-axis direction, the arrangement is not limited thereto. For example, the light-emitting elements can be arranged in a row that makes a certain angle with the Y-axis direction. Alternatively, the light-emitting elements can be arranged in a zigzag manner among a plurality of rows each being along the Y-axis direction. The light-emitting elements can be arranged in any manners so long as they are arranged at equal intervals in the Y-axis direction.

Furthermore, although in the above embodiment, the number of the light-emitting elements is equal to the number of the light-receiving elements, they can be unequal.

Moreover, although in the above embodiment, the lighting collective lens LEi is made up of one lens, the lighting collective lens LEi can be made up of two or more lenses.

Furthermore, in the above embodiment, if the sensitivity of detection is at a sufficient level without the light receiving optical system, the light receiving optical system may be omitted.

Moreover, although, in the above embodiment, the toner pattern on the transfer belt 2040 is detected, it is not limited thereto. Depending on the type of the image forming apparatus, the toner pattern on the photosensitive element or the intermediate transfer belt can be detected.

Suppose the case, for example, where, although a reflective optical sensor is used in an image forming apparatus, the reflective optical sensor is detached from the image forming apparatus and then attached to a different type of another image forming apparatus. The attachment position of the reflective optical sensor in this case is described below. In the reflective optical sensor, the area of the light-emitting surface of the light-emitting element Ei is S, the distance between the light-emitting element Ei and the lighting collective lens LEi is $L_0$, the distance between the lighting collective lens LEi and the focus position is $L_1$. Therefore, the lateral magnification m of the lighting collective lens LEi is $(L_1/L_0)$.

In this case, if the distance L between the lighting collective lens LEi and the transfer belt 2040 is less than the distance $L_1$, the spot size B on the transfer belt 2040 is larger than the spot size $(L_1/L_0)S$ on the focus position.

In this situation, because $L<L_1$, $(L/L_0)S<(L_1/L_0)S<B$ is satisfied. Moreover, because $B \leq P$ is preferable, $(L/L_0)S<P$ is preferable and thus $L/L_0<P/S$ is preferable. That is, if $L/L_0<P/S$ is satisfied, the above inequality (1) is also satisfied. Moreover, for the same reason described in the above embodiment, $L/L_0<10$ is preferable.

Suppose the case, for example, a reflective optical sensor with S=40 μm, P=400 μm, $L_0$=1 mm, and $L_1$=8 mm is attached to the different type of the image forming apparatus.

By setting L=5 mm, even when the toner pattern is small, at least one of an accurate position and an accurate toner density of the toner pattern is detectable.

Moreover, although, in the above embodiment, the image forming apparatus is the color printer 2000 that includes a plurality of photosensitive elements, the image forming apparatus can be some other devices, such as a printer that includes one photosensitive element and forms a single color image.

Furthermore, the image forming apparatus can be, not limited to printers, some other types of image forming apparatus such as a copier, facsimile machine, or a multifunction product (MFP).

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A reflective optical sensor configured to detect at least one of a position of the toner pattern or a toner density of a toner pattern, comprising:
    a light-emitting system that includes at least three light-emitting elements;
    a light-receiving system that includes at least three light-receiving elements and receives light emitted from the light-emitting system and then reflected by the toner pattern; and
    a lighting optical system that guides light emitted from the light-emitting system to the toner pattern,
    wherein the at least three light-emitting elements and the at least three light-receiving elements are arranged at equal intervals in a certain direction, and
    the lighting optical system has a lateral magnification m that satisfies m ≤P/S, where S is size of the light-emitting elements and P is arrangement pitch of the light-emitting elements.

2. The reflective optical sensor according to claim 1, wherein the lateral magnification m of the lighting optical system is less than 10.

3. The reflective optical sensor according to claim 1, further comprising a light receiving optical system that guides light reflected from the toner pattern to the light-receiving system in a convergent manner.

4. The reflective optical sensor according to claim 2, further comprising a light receiving optical system that guides light reflected from the toner pattern to the light-receiving system in a convergent manner.

5. The reflective optical sensor according to claim 3, wherein the lighting optical system includes at least three lighting collective lenses, wherein the individual lighting collective lenses correspond to the at least three light-emitting elements, and an optical axis of each of the at least three lighting collective lenses is parallel to an axis that passes through center of the corresponding light-emitting element and is perpendicular to the corresponding light-emitting element and the optical axis is shifted from the axis toward the light receiving optical system.

6. The reflective optical sensor according to claim 4, wherein the lighting optical system includes at least three lighting collective lenses, wherein the individual lighting collective lenses correspond to the at least three light-emitting elements, and an optical axis of each of the at least three lighting collective lenses is parallel to an axis that passes through center of the corresponding light-emitting element and is perpendicular to the corresponding light-emitting element and the optical axis is shifted from the axis toward the light receiving optical system.

7. The reflective optical sensor according to claim 3, wherein the light receiving optical system includes at least three light receiving collective lenses, wherein the individual light receiving collective lenses correspond to the at least three light-receiving elements, and an optical axis of each of the at least three light receiving collective lenses is parallel to an axis that both passes through center of the corresponding light-receiving element and is perpendicular to the corresponding light-receiving element and the optical axis is shifted from the axis toward the lighting optical system.

8. The reflective optical sensor according to claim 4, wherein the light receiving optical system includes at least three light receiving collective lenses, wherein the individual light receiving collective lenses correspond to the at least three light-receiving elements, and an optical axis of each of the at least three light receiving collective lenses is parallel to an axis that both passes through center of the corresponding light-receiving element and is perpendicular to the corresponding light-receiving element and the optical axis is shifted from the axis toward the lighting optical system.

9. The reflective optical sensor according to claim 5, wherein the light receiving optical system includes at least three light receiving collective lenses, wherein the individual light receiving collective lenses correspond to the at least three light-receiving elements, and an optical axis of each of the at least three light receiving collective lenses is parallel to an axis that both passes through center of the corresponding light-receiving element and is perpendicular to the corresponding light-receiving element and the optical axis is shifted from the axis toward the lighting optical system.

10. The reflective optical sensor according to claim 6, wherein the light receiving optical system includes at least three light receiving collective lenses, wherein the individual light receiving collective lenses correspond to the at least three light-receiving elements, and an optical axis of each of the at least three light receiving collective lenses is parallel to an axis that both passes through center of the corresponding light-receiving element and is perpendicular to the corresponding light-receiving element and the optical axis is shifted from the axis toward the lighting optical system.

11. An image forming apparatus comprising: an image carrier; an optical scanning device that scans the image carrier with a beam of light in a main-scanning direction, thereby forming a latent image, wherein the beam of light is modulated in accordance with image data; a developing device that forms a toner image by attaching toner to the latent image; a transferring device that transfers the toner image onto a medium; the reflective optical sensor according to claim 1 that detects at least one of the position and the toner density of the toner pattern formed on the image carrier or the medium.

12. The image forming apparatus according to claim 11, wherein the image data is multi-color image data.

* * * * *